(12) United States Patent
Li et al.

(10) Patent No.: US 10,202,401 B2
(45) Date of Patent: Feb. 12, 2019

(54) PROCESS FOR MAKING TETRACYCLIC HETEROCYCLE COMPOUNDS

(71) Applicants: Merck Sharp & Dohme. Corp., Rahway, NJ (US); MSD R&D (China) Co., Ltd., Pudong District, Shanghai (CN); Merck Sharp & Dohme Limited, Hoddesdon, Hertfordshire (GB)

(72) Inventors: Hongming Li, Westfield, NJ (US); Jingjun Yin, Greenbrook, NJ (US); Kevin M. Belyk, Metuchen, NJ (US); Kevin R. Campos, Berkeley Heights, NJ (US); Qinghao Chen, Edison, NJ (US); Alan M. Hyde, Metuchen, NJ (US); Tetsuji Itoh, Somerset, NJ (US); Artis Klapars, Edison, NJ (US); Matthew Thomas Tudge, Wayne, PA (US); Edward Cleator, Cambridge (GB); Aaron M. Dumas, Hertford (GB); Louis-Charles Campeau, Morris Plains, NJ (US); Yonggang Chen, Westfield, NJ (US); Ji Qi, Shanghai (CN); Wensong Xiao, Beijing (CN)

(73) Assignees: MSD R&D CN CO., LTD, Shanghai (CN); MERCK SHARP & DOHME CORP., Rahway, NJ (US); MERCK SHARP & DOHME LIMITED, Hoddesdon, Hertfordshire (GB)

( * ) Notice: Subject to any disclaimer, the term of this patent is extended or adjusted under 35 U.S.C. 154(b) by 0 days.

(21) Appl. No.: 15/807,992

(22) Filed: Nov. 9, 2017

(65) Prior Publication Data
US 2018/0065985 A1 Mar. 8, 2018

Related U.S. Application Data

(63) Continuation of application No. 15/325,392, filed as application No. PCT/CN2015/083786 on Jul. 10, 2015.

(60) Provisional application No. 62/171,012, filed on Jun. 4, 2015, provisional application No. 62/023,395, filed on Jul. 11, 2014.

(51) Int. Cl.
| | | |
|---|---|---|
| C07D 265/14 | (2006.01) |
| C07D 498/04 | (2006.01) |
| C07C 251/24 | (2006.01) |
| C07F 9/6509 | (2006.01) |
| C07F 17/02 | (2006.01) |
| C07D 413/14 | (2006.01) |
| C07D 239/74 | (2006.01) |
| C07D 413/04 | (2006.01) |
| C07D 417/04 | (2006.01) |
| C07D 265/36 | (2006.01) |

(52) U.S. Cl.
CPC .......... C07D 498/04 (2013.01); C07C 251/24 (2013.01); C07D 239/74 (2013.01); C07D 265/14 (2013.01); C07D 265/36 (2013.01); C07D 413/04 (2013.01); C07D 413/14 (2013.01); C07D 417/04 (2013.01); C07F 9/650994 (2013.01); C07F 17/02 (2013.01)

(58) Field of Classification Search
CPC .. C07D 498/04; C07D 251/24; C07D 239/74; C07D 265/14; C07D 265/36
USPC .................................................... 544/89
See application file for complete search history.

(56) References Cited

U.S. PATENT DOCUMENTS

2012/0083483 A1  4/2012 Coburn et al.

FOREIGN PATENT DOCUMENTS

WO  WO2012041014 A1  4/2012

OTHER PUBLICATIONS

Berge, S.M., et al.,, "Pharmaceutical Salts", J. Pharm. Sci, 1977, pp. 1-19, vol. 66, No. 1.
Gould, Salt Selections for Basic Drugs, Intl. J. Pharmaceutics, 1986, pp. 201-217, vol. 33.
Green & Wuts, Protective Groups in Organic Synthesis, 2nd Edition, 1991.
Vincze, et al, "The Palladium-Catylzed Preparation of Condensed Tetracyclic Heterocycles and Their Application to the Synthesis of rac-Mangochinine", Synthesis, 2006, pp. 1375-1385, No. 8.

*Primary Examiner* — Kahsay Habte
(74) *Attorney, Agent, or Firm* — Jeffrey P. Bergman; Catherine D. Fitch

(57) ABSTRACT

The present invention is directed to a process for making Tetracyclic Heterocycle Compounds of Formula (I):

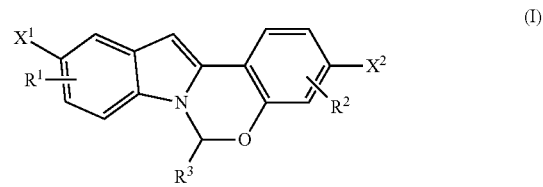

and pharmaceutically acceptable salts thereof, wherein $X^1$, $X^2$, $R^1$, $R^2$ and $R^3$ are defined above herein. The present invention is also directed to compounds that may be useful as synthetic intermediates in the process of the invention.

3 Claims, No Drawings

PROCESS FOR MAKING TETRACYCLIC HETEROCYCLE COMPOUNDS

CROSS-REFERENCE TO RELATED APPLICATIONS

This application is a continuation of application Ser. No. 15/325,392, filed Jan. 10, 2017, copending herewith, which is the national stage application under 35 U.S.C. 371 of International Patent Application No. PCT/CN2015/083786, filed Jul. 10, 2015, which claims priority to U.S. Provisional Patent Application No. 62/171,012, filed Jun. 4, 2015 and U.S. Provisional Patent Application No. 62/023,395, filed Jul. 11, 2014. Each of the aforementioned PCT and provisional applications is incorporated by reference in its entirety.

FIELD OF THE INVENTION

The present invention is directed to a process for preparing Tetracyclic Heterocycle Compounds which may be useful as intermediates for the synthesis of HCV NS5A inhibitors. The present invention is also directed to compounds that may be useful as synthetic intermediates in the process of the invention.

BACKGROUND OF THE INVENTION

Various substituted multicyclic heterocyclic compounds may be useful as pharmaceutical drugs, including inhibitors of the HCV NS5A enzyme. Included in these heterocycles is the tetracyclic heterocyclic core of dimethyl ((2S,2'S)-((2S, 2'S)-2,2'-(5,5'-((S)-6-phenyl-6H-benzo [5,6][1,3]oxazino[3, 4-a]indole-3,10-diyl)bis(1H-imidazole-5,2-diyl))bis(pyrrolidine-2,1-diyl))bis(3-methyl-1-oxobutane-2,1-diyl)) dicarbamate, as defined and described below. These compounds and pharmaceutically acceptable salts thereof may be useful in the treatment or prophylaxis of infection by HCV and in the treatment, prophylaxis, or delay in the onset or progression of HCV infection. Representative tetracyclic heterocyclic compounds that may be useful for treating HCV infection are described, for example, in US Patent Publication No. US20120083483.

US Patent Publication No. US20120083483 discloses methodology that can be employed to prepare such tetracyclic HCV NS5A inhibitors. This general methodology is illustrated immediately below:

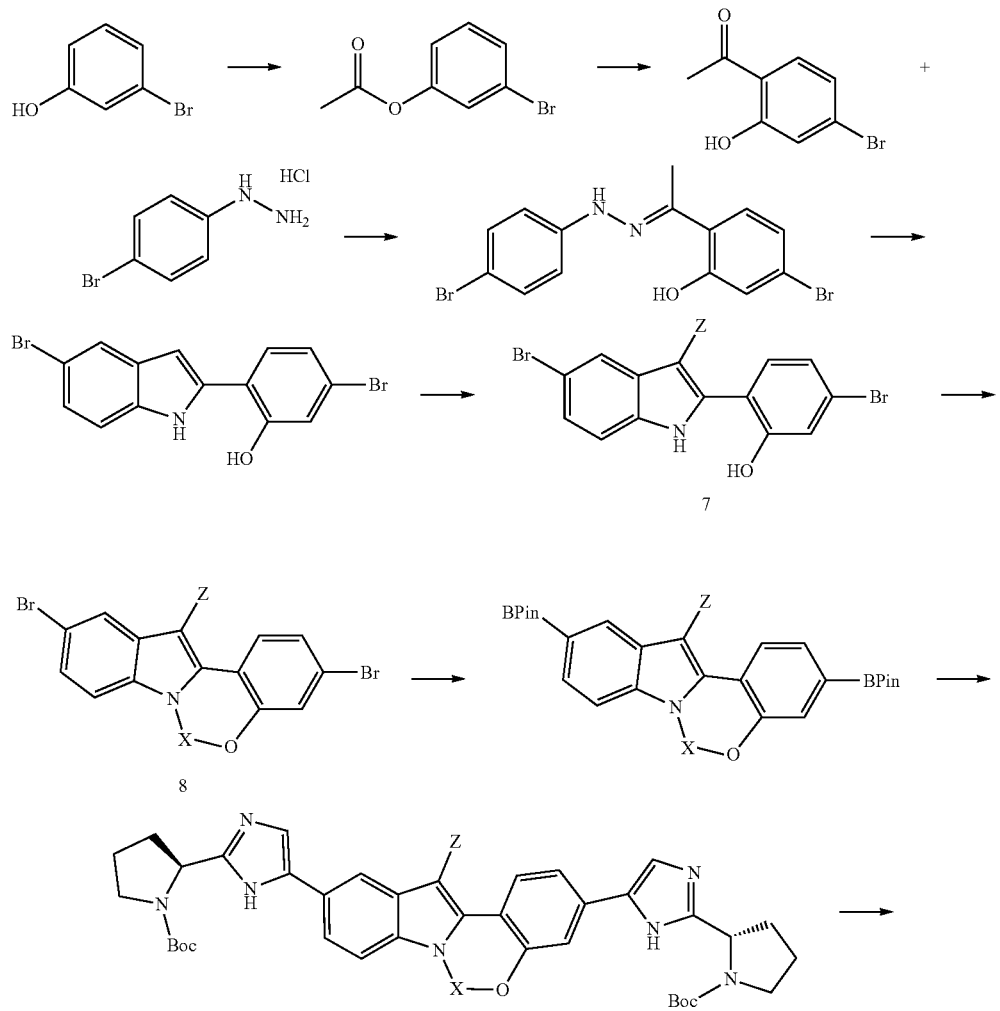

-continued

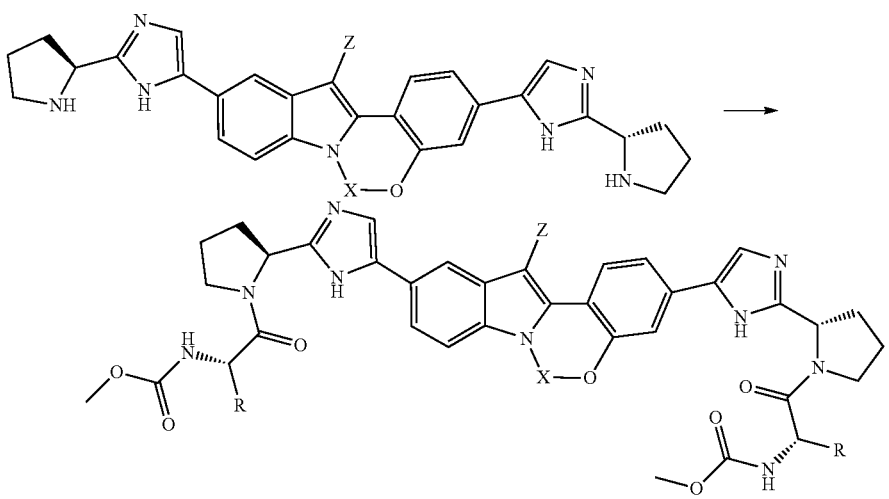

The methods described in US Patent Publication No. US20120083483 are practical routes for the preparation of tetracyclic heterocyclic compounds useful as HCV NS5A inhibitors. Nonetheless, there is always a need for alternative preparative routes which, for example, use reagents that are less expensive and/or easier to handle, consume smaller amounts of reagents, provide a higher yield of product, involve fewer steps, have smaller and/or more eco-friendly waste products, and/or provide a product of higher purity or higher enantiomeric excess.

SUMMARY OF THE INVENTION

The present invention is directed to a process (alternatively referred to herein as Process P) for preparing Compounds of Formula (I) (the "Tetracyclic Heterocycle Compounds")

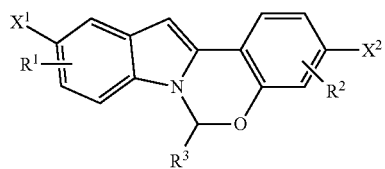

(I)

and pharmaceutically acceptable salts thereof, wherein said process comprises the steps:
(A) contacting a compound of Formula (II):

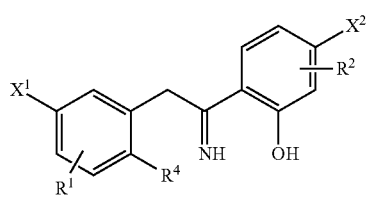

(II)

with a compound of formula (IIIa):

$R^3$—CHO     (IIIa)

or a compound of formula (IIIb):

$R^3$—CH=NR$^5$     (IIIb)

in the presence of an acid and an optional dehydrating agent, in an organic solvent A, for a time and at a temperature sufficient to form a compound of formula (IV):

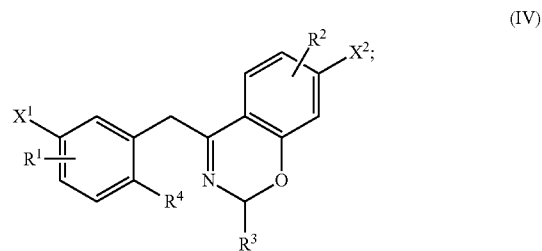

(IV)

and
(B) contacting the compound of formula (IV) with a transition metal catalyst in the presence of a base, in an organic solvent B, for a time and at a temperature sufficient to form a compound of formula (I),
wherein:
$X^1$ and $X^2$ are each independently selected from Cl, Br, I, OTf, OTs, OMs or OBs;
$R^1$ represents up to 3 optional ring substituent groups, which can be the same or different and are selected from —$C_1$-$C_6$ alkyl, halo, —OR$^5$, —C(O)R$^5$, —C(O)$_2$R$^5$, —NHC(O)R$^5$, —C(O)N(R$^5$)$_2$, —SR$^5$, —$C_1$-$C_6$ hydroxyalkyl, —$C_1$-$C_6$ haloalkyl, —N(R$^5$)$_2$, —S(O)R$^5$, —S(O)$_2$R$^5$, —CN and —NO$_2$;
$R^2$ represents up to 3 optional ring substituent groups, which can be the same or different and are selected from —$C_1$-$C_6$ alkyl, halo, —OR$^5$, —C(O)R$^5$, —C(O)$_2$R$^5$, —NHC(O)R$^5$, —C(O)N(R$^5$)$_2$, —SR$^5$, —$C_1$-$C_6$ hydroxyalkyl, —$C_1$-$C_6$ haloalkyl, —N(R$^5$)$_2$, —S(O)R$^5$, —S(O)$_2$R$^5$, —CN and —NO$_2$;
$R^3$ is $C_1$-$C_6$ alkyl, $C_6$-$C_{10}$ aryl, 5 or 6-membered monocyclic heteroaryl or 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can each be optionally and independently substituted with up to 3 groups, each independently selected from $C_1$-$C_6$ alkyl, $C_3$-$C_7$ cycloalkyl, halo, —$OR^5$, —$C(O)R^5$, —$C(O)_2R^5$, —$NHC(O)R^5$, —$C(O)N(R^5)_2$, —$SR^5$, —$C_1$-$C_6$ hydroxyalkyl, —$C_1$-$C_6$ haloalkyl, —$N(R^5)_2$, —$S(O)R^5$, —$S(O)_2R^5$, —CN and —$NO_2$; and $R^4$ is selected from Br, Cl, I, —OTf, —OMs, —OTs, —OBs, and —$OS(O)_2R^5$; and each occurrence of $R^5$ is independently selected from H, —$C_1$-$C_6$ alkyl, $C_3$-$C_7$ cycloalkyl, $C_6$-$C_{10}$ aryl, 5 or 6-membered monocyclic heteroaryl and 9 or 10-membered bicyclic heteroaryl.

Other embodiments, aspects and features of the present invention are either further described in or will be apparent from the ensuing description, examples, and appended claims.

DETAILED DESCRIPTION OF THE INVENTION

The present invention is directed to a process for preparing Tetracyclic Heterocycle Compounds of Formula (I) which may be useful as intermediates for making HCV NS5A inhibitors. One aspect of the present invention is the process comprising Steps A and B as set forth above in the Summary of the Invention (i.e., Process P).

Definitions and Abbreviations

The term "$C_1$-$C_6$ alkyl" as used herein, refers to an aliphatic hydrocarbon group, having from 1 to 6 carbon atoms wherein one of its hydrogen atoms is replaced with a bond. A $C_1$-$C_6$ alkyl group may be straight or branched and contain. Non-limiting examples of $C_1$-$C_6$ alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. A $C_1$-$C_6$ alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —$N(alkyl)_2$, —NH(cycloalkyl), —O—C(O)-alkyl, —O—C(O)-aryl, —O—C(O)-cycloalkyl, —C(O)OH and —C(O)O-alkyl. In one embodiment, a $C_1$-$C_6$ alkyl group is linear. In another embodiment, a $C_1$-$C_6$ alkyl group is branched. Unless otherwise indicated, a $C_1$-$C_6$ alkyl group is unsubstituted.

The term "$C_6$-$C_{10}$ aryl" refers to phenyl and naphthyl. In one embodiment, an aryl group is phenyl.

The term "3 to 7-membered cycloalkyl" refers to a non-aromatic mono- or ring system comprising from about 3 to about 7 ring carbon atoms. Examples of "3 to 7-membered cycloalkyl" groups include cyclopropyl, cyclobutyl, cyclopentyl, cyclohexyl and cycloheptyl. A 3 to 7-membered cycloalkyl group can be optionally substituted with one or more "ring system substituents" which may be the same or different, and are as defined herein below. In one embodiment, a 3 to 7-membered cycloalkyl group is unsubstituted. A ring carbon atom of a 3 to 7-membered cycloalkyl may be functionalized as a carbonyl group. An illustrative example of such a 3 to 7-membered cycloalkyl (also referred to herein as a "cycloalkanoyl" group) includes, but is not limited to, cyclobutanoyl:

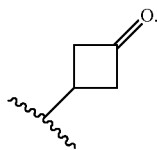 [SMILES: *C1CC(=O)C1]

The term "halo" as used herein, refers to fluorine, chlorine, bromine and iodine (alternatively referred to as fluoro, chloro, bromo, and iodo).

The term "5 or 6-membered monocyclic heteroaryl," as used herein, refers to an aromatic monocyclic ring system comprising about 5 to about 6 ring atoms, wherein from 1 to 4 of the ring atoms is independently O, N or S and the remaining ring atoms are carbon atoms. A 5 or 6-membered monocyclic heteroaryl group can be optionally substituted by one or more "ring system substituents" which may be the same or different, and are as defined herein below. A 5 or 6-membered monocyclic heteroaryl group is joined via a ring carbon atom, and any nitrogen atom of a heteroaryl can be optionally oxidized to the corresponding N-oxide. The term "5 or 6-membered monocyclic heteroaryl" also encompasses a 5 or 6-membered monocyclic heteroaryl group, as defined above, which is fused to a benzene ring. Non-limiting examples of 5 or 6-membered monocyclic heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, benzofurazanyl, indolyl, azaindolyl, benzimidazolyl, benzothienyl, imidazolyl, benzimidazolyl, thienopyridyl, thienopyrimidyl, pyrrolopyridyl, imidazopyridyl, isoquinolinyl, 1,2,4-triazinyl, benzothiazolyl and the like, and all isomeric forms thereof. Unless otherwise indicated, a 5 or 6-membered monocyclic heteroaryl group is unsubstituted.

The term "9 or 10-membered bicyclic heteroaryl," as used herein, refers to an aromatic bicyclic ring system comprising about 9 to about 10 ring atoms, wherein from 1 to 4 of the ring atoms is independently O, N or S and the remaining ring atoms are carbon atoms. A 9 or 10-membered bicyclic heteroaryl group can be optionally substituted by one or more "ring system substituents" which may be the same or different, and are as defined herein below. A 9 or 10-membered bicyclic heteroaryl group is joined via a ring carbon atom, and any nitrogen atom of a heteroaryl can be optionally oxidized to the corresponding N-oxide. Non-limiting examples of 9 or 10-membered bicyclic heteroaryls include and the like, and all isomeric forms thereof. Unless otherwise indicated, a 9 or 10-membered bicyclic heteroaryl group is unsubstituted.

The term "transition metal catalyst," as used herein, refers to a complex comprising a transition metal and one or more ligands, which are independently selected from any organic and/or any inorganic ligands.

The term "phenol protecting group," as used herein, refers to a group that can be used to protect the hydroxyl group of a phenol moiety from reacting during any chemical reactions that take place in the presence of said phenol protecting group. Non-limiting examples of phenol protecting groups include organosilyl groups, such as trimethylsilyl (TMS) and t-butyldimethylsilyl (TBDMS); alkyl groups; benzyl; allyl; and those recognized by those with ordinary skill in the art as well as those disclosed in standard textbooks such as, for example, T. W. Greene et al, *Protective Groups in Organic Synthesis* (1991), Wiley, New York.

Unless expressly stated to the contrary in a particular context, any of the various cyclic rings and ring systems described herein may be attached to the rest of the compound of which they are a part at any ring atom (i.e., any carbon atom or any heteroatom) provided that a stable compound results.

Unless expressly stated to the contrary, all ranges cited above are inclusive; i.e., the range includes the values for the upper and lower limits of the range as well as all values in between.

When any variable occurs more than one time in a compound involved in the process of the invention (e.g., $R^1$ or $R^2$), its definition on each occurrence is independent of its definition at every other occurrence. Also, combinations of substituents and/or variables are permissible only if such combinations result in a stable compound.

Unless expressly stated to the contrary, substitution by a named substituent is permitted on any atom in a ring (e.g., cycloalkyl, aryl, or heteroaryl) provided such ring substitution is chemically allowed and results in a stable compound.

In reference to the compounds employed as reactants or reagents in the process of the invention (e.g., Compounds II, III, and IV), a "stable" compound is one whose structure and properties remain or can be caused to remain essentially unchanged for a period of time sufficient to allow its use in the process of the invention so as to achieve the preparation of Compound of Formula (I). In reference to Compound of Formula (I), a "stable" compound is a compound which can be prepared in accordance with the process of the present invention and then isolated and whose structure and properties remain or can be caused to remain essentially unchanged for a period of time sufficient to allow use of the compound for its intended purpose; e.g., for use as a synthetic intermediate to make medicinally useful compounds, such as compounds useful for treating HCV infection in a subject.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

The Tetracyclic Heterocycle Compounds can form salts which are also within the scope of this invention. Reference to a Tetracyclic Heterocycle Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Tetracyclic Heterocycle Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Tetracyclic Heterocycle Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the Tetracyclic Heterocycle Compounds may be atropisomers (e.g., substituted biaryls) and are considered as part of this invention. Enantiomers can also be directly separated using chiral chromatographic techniques.

It is also possible that the Tetracyclic Heterocycle Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Tetracyclic Heterocycle Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

The following abbreviations are used below and have the following meanings: Ac is acetate, Boc or BOC is t-butoxy carbonyl, Bs is besyl (benzenesulfonyl), t-Bu is tertiary butyl, n-Bu is n-butyl, dba is dibenzylideneacetone, DCM is dichloromethane, DMA is N,N-dimethylacetamide, DME is dimethoxyethane, EtOAc is ethyl acetate, HPLC is high performance liquid chromatography, Me is methyl, Ms is mesyl (methanesulfonyl), Tf is triflate (trifluoromethanesulfonyl), TFA is trifluoroacetic acid, TLC is thin-layer chromatography, and Ts is tosyl (p-toluenesulfonyl).

The Processes of the Present Invention

The present invention is directed to a process for preparing Tetracyclic Heterocycle Compounds of Formula (I) which may be useful as synthetic intermediates for the synthesis of HCV NS5A inhibitors. One aspect of the present invention is the process comprising Steps A and B as set forth above in the Summary of the Invention (i.e., Process P).

In another aspect, the present invention provides each individual step of Process P as a separate and individual embodiment (e.g. in one embodiment the present invention provides the process illustrated in Step A of Process P; in another embodiment the present invention provides the process illustrated in Step B of Process P)

In one embodiment, for Process P, step A, the compound of formula (II) is reacted with a compound of formula (IIIa).

In another embodiment, for Process P, step A, the compound of formula (II) is reacted with a compound of formula (IIIb).

In one embodiment, for Process P, each occurrence of $R^1$ and $R^2$ is independently H or halo.

In another embodiment, for Process P, each occurrence of $R^1$ and $R^2$ is independently H or F.

In another embodiment, for Process P, each occurrence of $R^1$ is H and each occurrence of $R^2$ is independently H or F.

In one embodiment, for Process P, $R^3$ is 5 or 6-membered heteroaryl or $C_6$-$C_{10}$ aryl, wherein $R^3$ can be optionally substituted with a group selected from $C_1$-$C_6$ alkyl and $C_3$-$C_7$ cycloalkyl.

In another embodiment, for Process P, $R^3$ is phenyl.

In another embodiment, for Process P, $R^3$ is 5-membered heteroaryl, which can be optionally substituted with a group selected from $C_1$-$C_6$ alkyl and $C_3$-$C_7$ cycloalkyl.

In another embodiment, for Process P, $R^3$ is thiophenyl or thiazolyl, either of which can be optionally substituted with a $C_1$-$C_6$ alkyl group or a $C_3$-$C_7$ cycloalkyl group.

In still another embodiment, for Process P, $R^3$ is thiophenyl or thiazolyl, either of which can be optionally substituted with a $C_3$-$C_7$ cycloalkyl group.

In another embodiment, for Process P, $R^3$ is thiophenyl or thiazolyl, either of which can be optionally substituted with a $C_3$-$C_7$ cyclopropyl group.

In one embodiment, for Process P, $X^1$ and $X^2$ are each —Cl.

In another embodiment, for Process P, $R^4$ is —Br.

In one embodiment, for Process P, each occurrence of $R^1$ and $R^2$ is independently H or halo and $R^3$ is 5 or 6-membered heteroaryl or $C_6$-$C_{10}$ aryl, wherein $R^3$ can be optionally substituted with a group selected from $C_1$-$C_6$ alkyl and $C_3$-$C_7$ cycloalkyl.

In another embodiment, for Process P, each occurrence of $R^1$ and $R^2$ is independently H or halo; $R^3$ is 5 or 6-membered heteroaryl or $C_6$-$C_{10}$ aryl, wherein $R^3$ can be optionally substituted with a group selected from $C_1$-$C_6$ alkyl and $C_3$-$C_7$ cycloalkyl; $R^4$ is Br; and $X^1$ and $X^2$ are each —Cl.

In another embodiment, for Process P, each occurrence of $R^1$ is H; each occurrence of $R^2$ is independently H or halo; $R^3$ is phenyl, thiophenyl or thiazolyl, any of which can be optionally substituted with a $C_1$-$C_6$ alkyl group or a $C_3$-$C_7$ cycloalkyl group; $R^4$ is Br; and $X^1$ and $X^2$ are each —Cl.

In one embodiment, for Process P:
the organic solvent A is selected from toluene, dichloromethane, benzene, tetrahydrofuran, 2-methyl tetrahydrofuran, ethyl acetate and acetonitrile;
the acid employed in Step A is an organic acid;
Step A is conducted at a temperature in a range of from about 0° C. to about 100° C.;
the organic solvent B is selected from toluene, dimethylacetamide, dioxane, acetonitrile, tetrahydrofuran, t-amyl alcohol, benzene, xylenes, N,N-dimethylformamide, dichlororomethane and dimethoxyethane;
the transition metal catalyst employed in Step B, is selected from an organopalladium, organocopper, organonickel or organoiron compound that is bound to a chiral ligand;
the base employed in step B is selected from a carbonate base, a phosphate base, a fluoride base, an acetate base, a bicarbonate base and a hydroxide base; and
Step B is conducted at a temperature in a range of from about 0° C. to about 120° C.

In another embodiment, for Process P:
the organic solvent A is toluene or dichloromethane;
the acid employed in Step A is trifluoroacetic acid or camphorsulfonic acid;
Step A is conducted at a temperature in a range of from about 25° C. to about 65° C.;
the organic solvent B is toluene or dimethoxyethane;
the transition metal catalyst employed in Step B, is an organopalladium compound that is bound to a chiral ligand;
the base employed in step B is a phosphate base; and
Step B is conducted at a temperature in a range of from about 30° C. to about 70° C.

In another embodiment, for Process P:
the organic solvent A is toluene, MeTHF, or dichloromethane;
the acid employed in Step A is trifluoroacetic acid, trifluoromethylsulfonic acid, TMSOTf, or camphorsulfonic acid;
Step A is conducted at a temperature in a range of from about 0° C. to about 65° C.;
the organic solvent B is N,N-dimethylacetamide, toluene, or acetonitrile;
the transition metal catalyst employed in Step B, is an organocopper compound;
the base employed in step B is a carbonate base or a phosphate base; and Step B is conducted at a temperature in a range of from about 25° C. to about 100° C.

In another embodiment, the present invention provides a process ("Process A") for preparing a compound of Formula (Ia):

(Ia)

[Chemical structure of Formula (Ia)]

wherein said process comprises the steps:
(A) contacting a compound of Formula (II):

(II)

[Chemical structure of Formula (II)]

with a compound of formula (IIIa):

R³—CHO          (IIIa)

in the presence of an acid in an organic solvent, and an optional dehydrating agent, for a time and at a temperature sufficient to form a compound of formula (IV):

(IV)

[Chemical structure of Formula (IV)]

and
(B) contacting the compound of formula (IV) with a transition metal catalyst in the presence of a base, in an organic solvent B, for a time and at a temperature sufficient to form a compound of formula (I),
wherein:
$R^1$ represents up to 3 optional ring substituent groups, which can be the same or different and are selected from —$C_1$-$C_6$ alkyl and halo;
$R^2$ represents up to 3 optional ring substituent groups, which can be the same or different and are selected from —$C_1$-$C_6$ alkyl and halo;
$R^3$ is $C_1$-$C_6$ alkyl, $C_6$-$C_{10}$ aryl or 5 or 6-membered monocyclic heteroaryl, wherein said $C_6$-$C_{10}$ aryl group, and said 5 or 6-membered monocyclic heteroaryl group can each be optionally and independently substituted with up to 2 groups, each independently selected from $C_1$-$C_6$ alkyl and $C_3$-$C_7$ cycloalkyl.

In one embodiment, for Process A:
the organic solvent A is toluene or dichloromethane;
the acid employed in Step A is camphorsulfonic acid or TFA;
Step A is conducted at a temperature in a range of from about 20° C. to about 70° C.;
the organic solvent B is toluene;
the transition metal catalyst employed in Step B, is an organopalladium compound that is bound to a chiral ligand;
the base employed in step B is a phosphate base;
Step B is conducted at a temperature in a range of from about 30° C. to about 70° C.

In another embodiment, for Process A:
the organic solvent A is toluene or dichloromethane;
the acid employed in Step A is camphorsulfonic acid or TFA;
Step A is conducted at a temperature in a range of from about 40° C. to about 65° C.;
the organic solvent B is toluene;
the transition metal catalyst employed in Step B, is an organopalladium compound that is bound to a chiral ligand, wherein said chiral ligand has the formula:

[Chemical structures of chiral ligands]

the base employed in step B is $K_3PO_4$;
Step B is conducted at a temperature in a range of from about 40° C. to about 60° C.

In another embodiment, the present invention provides a process ("Process B") for preparing a compound of Formula (Ia):

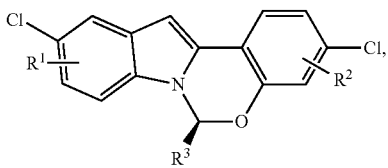

wherein said process comprises the steps:

(A) contacting a compound of Formula (IIa):

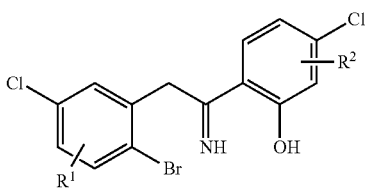

with a compound of formula (IIIb):

$R^3$—CH=$NR^5$ (IIIb)

in the presence of an acid in an organic solvent A, and an optional dehydrating agent, for a time and at a temperature sufficient to form a compound of formula (IV):

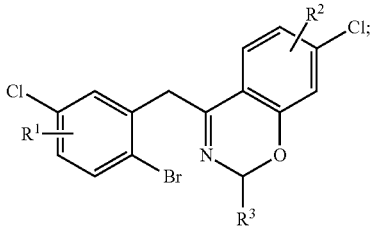

and (B) contacting the compound of formula (IV) with a transition metal catalyst in the presence of a base, in an organic solvent B, for a time and at a temperature sufficient to form a compound of formula (I),
wherein:

$R^1$ represents up to 3 optional ring substituent groups, which can be the same or different and are selected from —$C_1$-$C_6$ alkyl and halo;

$R^2$ represents up to 3 optional ring substituent groups, which can be the same or different and are selected from —$C_1$-$C_6$ alkyl and halo;

$R^3$ is $C_1$-$C_6$ alkyl, $C_6$-$C_{10}$ aryl or 5 or 6-membered monocyclic heteroaryl, wherein said $C_6$-$C_{10}$ aryl group, and said 5 or 6-membered monocyclic heteroaryl group can each be optionally and independently substituted with up to 2 groups, each independently selected from $C_1$-$C_6$ alkyl and $C_3$-$C_7$ cycloalkyl; and $R^5$ is $C_1$-$C_6$ alkyl or phenyl.

In one embodiment, for Process B:
the organic solvent A is toluene;
the acid employed in Step A is TFA;
Step A is conducted at a temperature in a range of from about 10° C. to about 40° C.;
the organic solvent B is toluene;
the transition metal catalyst employed in Step B, is an organopalladium compound that is bound to a chiral ligand;
the base employed in step B is a phosphate base; and
Step B is conducted at a temperature in a range of from about 30° C. to about 70° C.

In another embodiment, for Process B:
the organic solvent A is toluene;
the acid employed in Step A is TFA;
Step A is conducted at a temperature in a range of from about 20° C. to about 30° C.;
the organic solvent B is toluene;
the transition metal catalyst employed in Step B, is an organopalladium compound that is bound to a chiral ligand, wherein said chiral ligand has the formula:

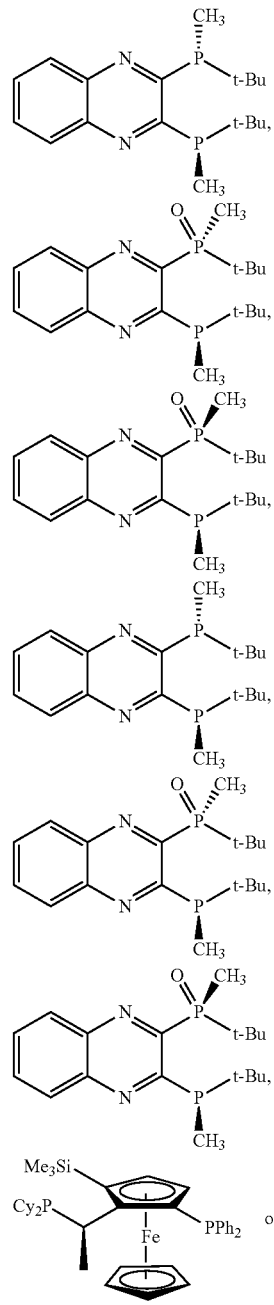

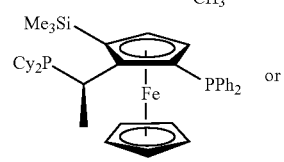

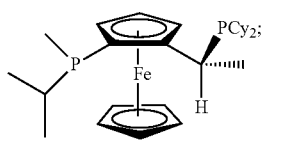

the base employed in step B is $K_3PO_4$; and

Step B is conducted at a temperature in a range of from about 40° C. to about 60° C.

In one embodiment, for Processes A, B and P, the base employed in Step B is selected from $KHCO_3$, $Na_2CO_3$, $Cs_2CO_3$, $K_2CO_3$, $Na_3PO_4$, $K_3PO_4$, $Na_2PO_4$ and $K_2PO_4$.

In another embodiment, for Processes A, B and P, the base employed in Step B is $K_3PO_4$.

In one embodiment, for Processes A, B and P, the ligands used in the transition metal catalyst employed in Step B are selected from one or more of: dba, chalcone, (R,R)-QuinoxP, (R,S)-QuinoxP, (S,R)-QuinoxP, (S,S)-QuinoxP, halo, —OAc, (S)-BINAPINE, (R)-Quinap, (R)—N-PINAP85, SL-J210-1, (R)—(S)-xyl2P-Fc-PtBu$_2$, —(S)-tBu-PHOX, (S)-tBuO-Tol-PHOX, (S)—(S)-Ph2P-Fc-tBu-oxazoline, SL-N004, (Sa,S)-DTB-Bn-SIPHOX, ChenPhos SL-356-1, (S)-f-Binaphane, SL-J001-1, SL-J204-1, SL-J304-1, (R)-BINAP, (R)-SEGPHOS, (R)—P-Phos, (R)-DTBM-SEG-PHOS, (S)-DTBM-Garphos, (S)-DTBM-MeO-BIPHEP, (R)-3,5-tBuPh-MeO-BIPHEP, (R)-3,5-iPr-4-Me2NPh-MeO-BIPHEP, SL-J001-1, SL-J204-1, SegPhos, MeO-BI-PHEP, GarPhos, SL-J304-1 and 3,5-di-t-butyl-4-methoxybenzene.

In another embodiment, for Processes A, B and P, the ligand used in the transition metal catalyst employed in Step B is (R,R)-QuinoxP.

In still another embodiment, for Processes A, B and P, a ligand used in the transition metal catalyst employed in Step B is (R,S)-QuinoxP.

In another embodiment, for Processes A, B and P, the ligand used in the transition metal catalyst employed in Step B is (S,R)-QuinoxP.

In yet another embodiment, for Processes A, B and P, a ligand used in the transition metal catalyst employed in Step B is (S,S)-QuinoxP.

In another embodiment, for Processes A, B and P, the ligand used in the transition metal catalyst employed in Step B is selected from:

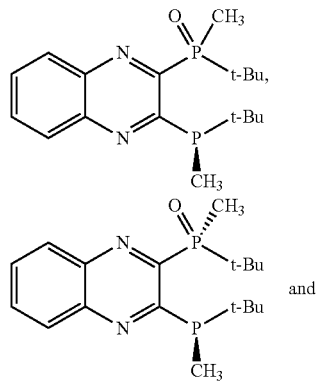

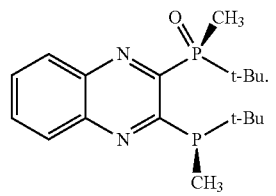

In still another embodiment, for Processes A, B and P, the ligand used in the transition metal catalyst employed in Step B is:

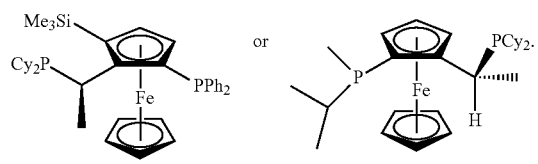

In one embodiment, for Processes A, B and P, in step A, the optional dehydrating agent is absent.

In another embodiment, for Processes A, B and P, in step A, the optional dehydrating agent is present.

In another embodiment, for Processes A, B and P, in step A, the optional dehydrating agent is present and is selected from molecular sieves, trimethylsilyl chloride and magnesium sulfate.

In still another embodiment, for Processes A, B and P, in step A, the optional dehydrating agent is present and is molecular sieves.

In one embodiment, for Processes A, B and P, the compound of formula (I) being made is:

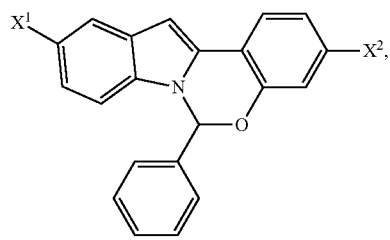

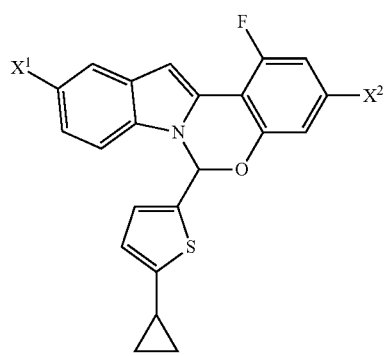

or

-continued
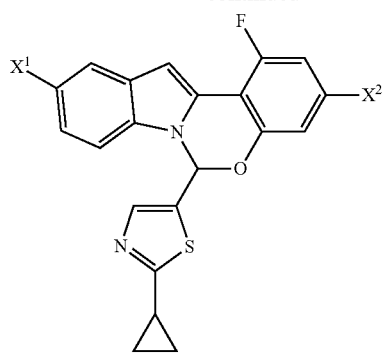
wherein each occurrence of $X^1$ is independently selected from Br, Cl and I and each occurrence of $X^2$ is independently selected from Br, Cl and I.
In another embodiment, for Processes A, B and P, the compound of formula (I) being made is:
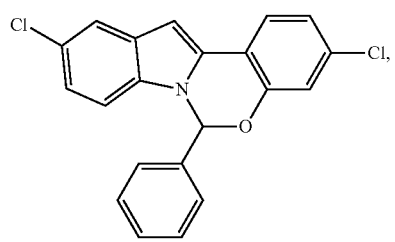
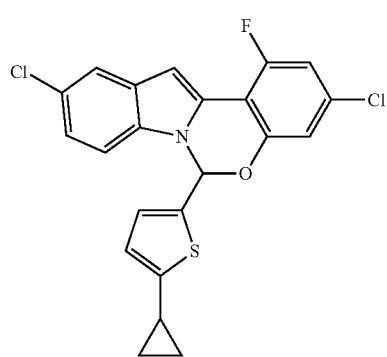
or
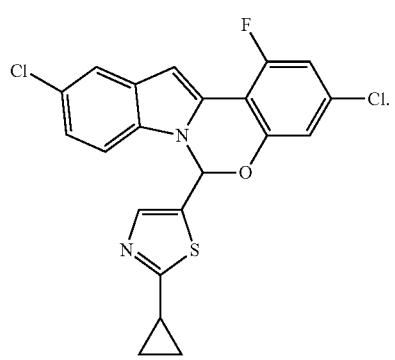
In another embodiment, for Processes A, B and P, the compound of formula (I) being made is:
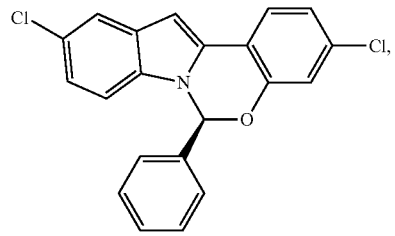
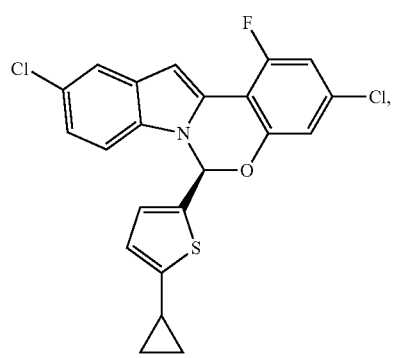 [SMILES: Fc1cc(Br)cc2c1-c1cc3cc(Cl)ccc3n1[C@H](c1cnc(C3CC3)s1)O2]
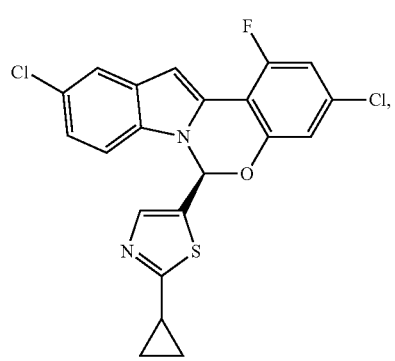
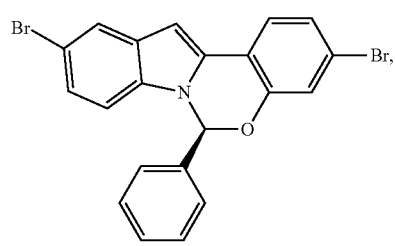
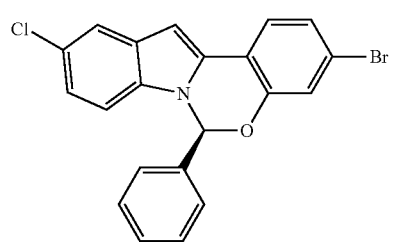
or -continued

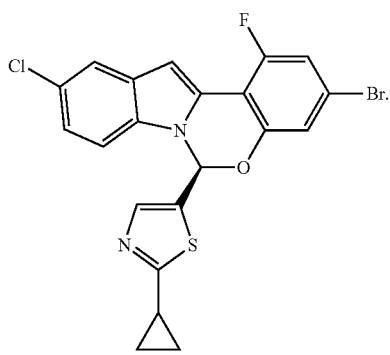

In one embodiment, the present invention provides a compound of formula (IV):

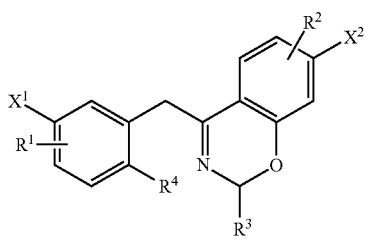

or a pharmaceutically acceptable salt thereof,
wherein:
$X^1$ and $X^2$ are each independently selected from Cl, Br, I, OTf, OTs, OMs or OBs;
$R^1$ represents up to 3 optional ring substituent groups, which can be the same or different and are selected from —$C_1$-$C_6$ alkyl, halo, —$OR^6$, —$C(O)R^6$, —$C(O)_2R^6$, —$NHC(O)R^6$, —$C(O)N(R^6)_2$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$;
$R^2$ represents up to 3 optional ring substituent groups, which can be the same or different and are selected from —$C_1$-$C_6$ alkyl, halo, —$OR^6$, —$C(O)R^6$, —$C(O)_2R^6$, —$NHC(O)R^6$, —$C(O)N(R^6)_2$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$;
$R^3$ is $C_1$-$C_6$ alkyl, $C_6$-$C_{10}$ aryl, 5 or 6-membered monocyclic heteroaryl or 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can each be optionally and independently substituted with one or more $R^5$ groups; and
$R^4$ is selected from Br, Cl, I, —OTf, —OMs, —OTs, —OBs, and —$OS(O)_2R^6$;
each occurrence of $R^5$ is independently selected from $C_1$-$C_6$ alkyl, $C_3$-$C_7$ cycloalkyl, halo, —$OR^6$, —$C(O)R^6$, —$C(O)_2R^6$, —$NHC(O)R^6$, —$C(O)N(R^6)_2$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$; and
each occurrence of $R^6$ is independently selected from H, —$C_1$-$C_6$ alkyl, $C_3$-$C_7$ cycloalkyl, $C_6$-$C_{10}$ aryl, 5 or 6-membered monocyclic heteroaryl and 9 or 10-membered bicyclic heteroaryl.

In another embodiment, the present invention provides a compound of formula (IVa):

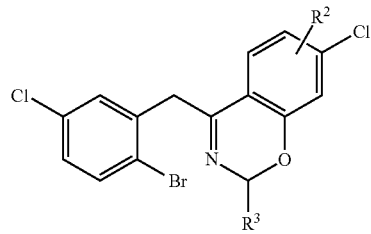

or a pharmaceutically acceptable salt thereof,
wherein:
$R^2$ represents an optional ring substituent group, which is —$C_1$-$C_6$ alkyl or halo; and
$R^3$ is $C_6$-$C_{10}$ aryl or 5 or 6-membered monocyclic heteroaryl wherein said $C_6$-$C_{10}$ aryl group and said 5 or 6-membered monocyclic heteroaryl can each be optionally and independently substituted with $C_1$-$C_6$ alkyl, halo or $C_3$-$C_7$ cycloalkyl.

In one embodiment, the present invention provides a compound having the structure:

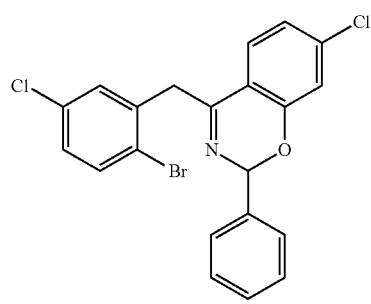

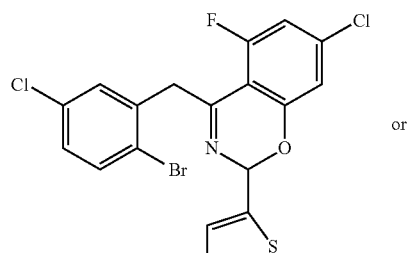
or

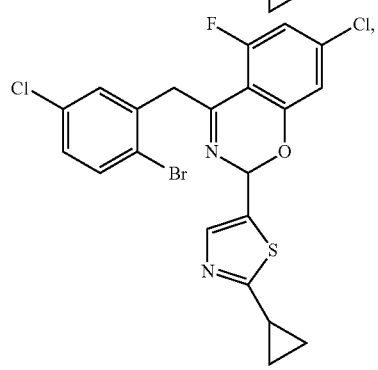

or a pharmaceutically acceptable salt thereof.

In another embodiment, the present invention provides a compound having the structure:

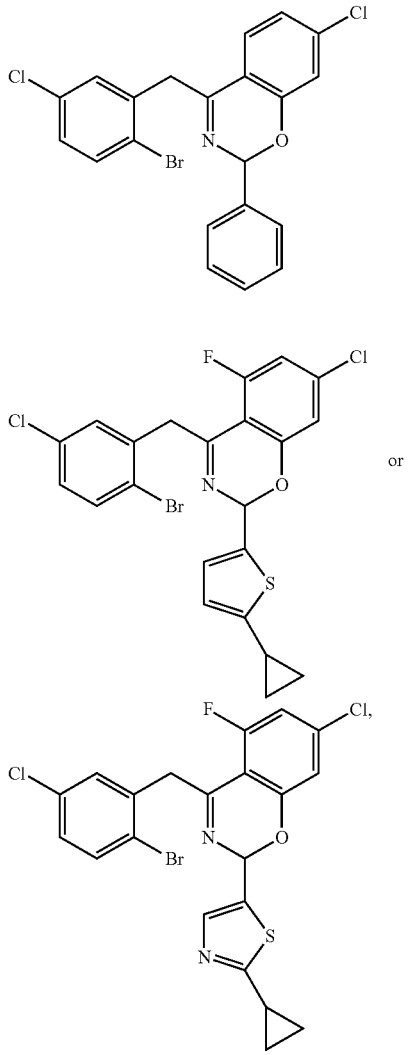

or a pharmaceutically acceptable salt thereof.

In another embodiment, the present invention provides a compound having the formula (V):

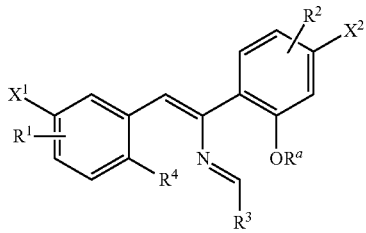

(V)

or a pharmaceutically acceptable salt thereof,
wherein:

$X^1$ and $X^2$ are each independently selected from Cl, Br, I, —OTf, —OTs, —OMs or —OBs;

$R^a$ is selected from H, acyl, —C(O)O—($C_1$-$C_6$ alkyl), allyl, benzyl, a metal cation and a phenol protecting group;

$R^1$ represents up to 3 optional ring substituent groups, which can be the same or different and are selected from —$C_1$-$C_6$ alkyl, halo, —$OR^6$, —$C(O)R^6$, —$C(O)_2R^6$, —$NHC(O)R^6$, —$C(O)N(R^6)_2$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$;

$R^2$ represents up to 3 optional ring substituent groups, which can be the same or different and are selected from —$C_1$-$C_6$ alkyl, halo, —$OR^6$, —$C(O)R^6$, —$C(O)_2R^6$, —$NHC(O)R^6$, —$C(O)N(R^6)_2$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$;

$R^3$ is $C_1$-$C_6$ alkyl, $C_6$-$C_{10}$ aryl, 5 or 6-membered monocyclic heteroaryl or 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can each be optionally and independently substituted with one or more $R^5$ groups; and $R^4$ is selected from Br, Cl, I, —OTf, —OMs, —OTs, —OBs, and —$OS(O)_2R^6$;

each occurrence of $R^5$ is independently selected from $C_1$-$C_6$ alkyl, $C_3$-$C_7$ cycloalkyl, halo, —$OR^6$, —$C(O)R^6$, —$C(O)_2R^6$, —$NHC(O)R^6$, —$C(O)N(R^6)_2$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$; and each occurrence of $R^6$ is independently selected from H, —$C_1$-$C_6$ alkyl, $C_3$-$C_7$ cycloalkyl, $C_6$-$C_{10}$ aryl, 5 or 6-membered monocyclic heteroaryl and 9 or 10-membered bicyclic heteroaryl.

In one embodiment, the present invention provides a compound having the structure:

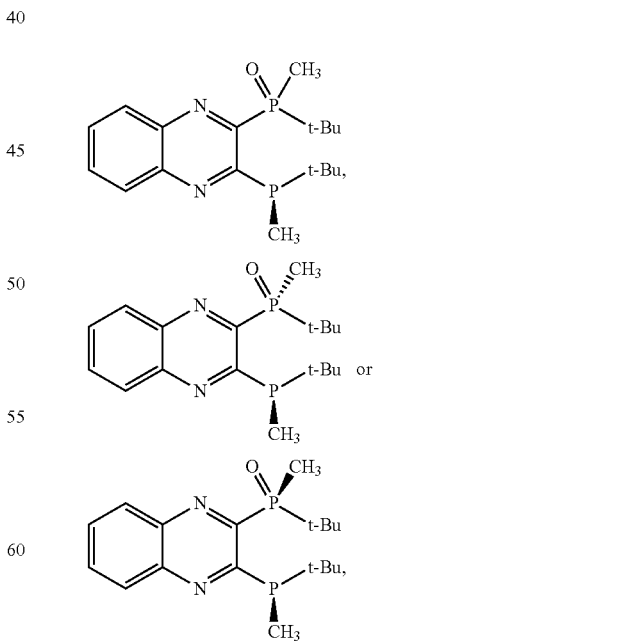

In another embodiment, the present invention provides a compound having the structure:

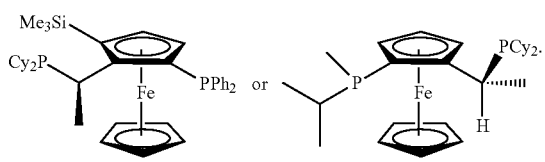

In one embodiment, any step of any of the processes described herein can be conducted in any organic solvent.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Ultrashield 400 (400 MHz) and are reported as ppm downfield from Me$_4$Si with number of protons, multiplicities, and coupling constants in Hertz indicated parenthetically. Where LC/MS data are presented, analyses was performed using an Agilent 1100 LCMS system with LC column: Ascentis Express C18, 2.7 micron, 150 mm×3 mm ID; gradient flow: 0 minutes—10% CH$_3$CN/2 mM aqueous NH$_4$COOH/HCOOH, 6 minutes—95% CH$_3$CN, 6-12 minutes—95% CH$_3$CN, 14 minutes—stop. The observed parent ion is given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Compound 5

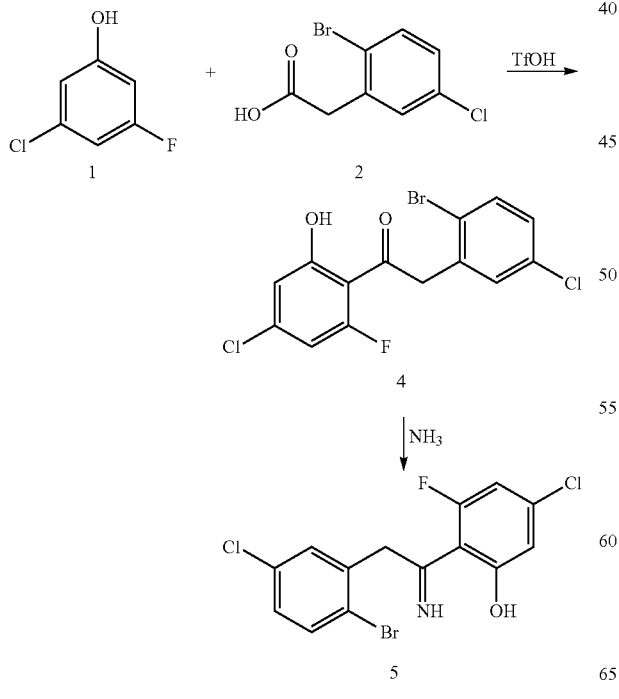

Step A: Synthesis of Compound 4

3-chloro-5-fluorophenol (1, 98 wt %, 10.0 g, 66.9 mmol) and 2-(2-bromo-5-chlorophenyl)acetic acid (2, 20.02 g, 80.0 mmol) were mixed with TfOH (91 mL) and heated to 60° C. under an nitrogen atmosphere. After stirring at this temperature for 16 hours, the mixture was cooled to room temperature and poured over a 20 minute period into isopropanol (500 mL) that had been cooled in an ice/water bath. The resulting slurry was diluted with water (125 mL), which was added over 10 minutes. After aging for 30 minutes in the ice/water bath, the mixture was filtered, and the collected solid was washed with 4:1 isopropanol/water (50 mL). The solid was dried in vacuo to provide compound 4 (20.14 g, 53.3 mmol, 80% yield).

Step B: Synthesis of Compound 5

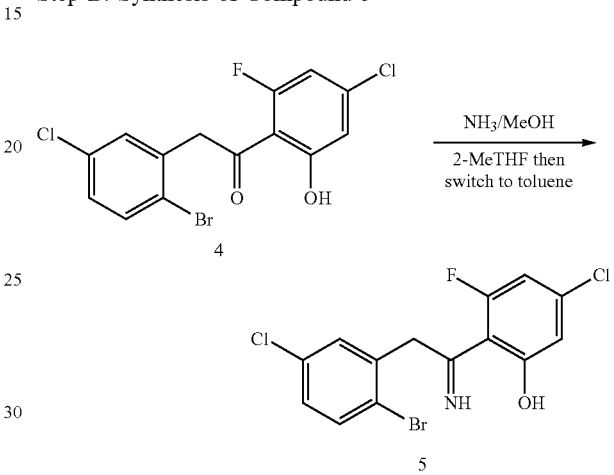

Compound 4 (2.03 g, 5.37 mmol) was taken up in 2-methyltetrahydrofuran (20.3 mL, 10 volumes), and to this solution was added ammonia in methanol (11.51 mL of 7N, 81 mmol, 15 eq.). The resulting solution was aged at room temperature for 16 hours, then concentrated by the removal of 25 mL of solvent and the slurry was treated with toluene (70 mL). The resulting solution was then redistilled to remove a further 35 mL of solvent and achieve a final solution of the imine in 20 volumes of toluene. This solution was used without further purification. A sample of this solution was analyzed and found to contain a 97.5:2.5 ratio of compound 5:compound 4.

Example 2

Preparation of Compound 7

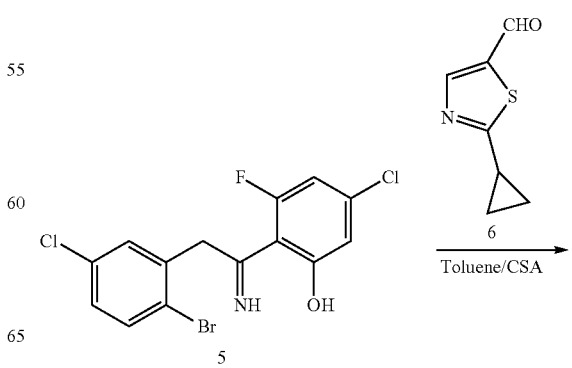

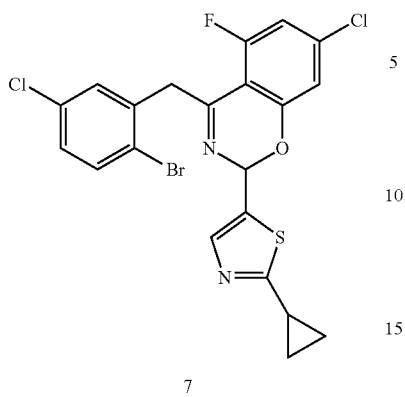

7

Compound 6 (0.58 g, 3.79 mmol, 1.1 eq.) was taken up in toluene (20 mL), (±)-camphorsulphonic acid (0.16 g, 0.69 mmol, 0.2 eq.) was added and the resulting solution was heated to 60° C. To this solution was added compound 5 (1.30 g, 3.45 mmol) as a solution in toluene (26 mL, 20 volumes) over a 1 hour period while distilling the reaction mixture at an equal rate to remove toluene (26 mL). The final solution was aged for an additional 2 hours then cooled to room temperature and treated with triethylamine (0.087 g, 0.862 mmol, 0.25 eq.). The resulting solution was then washed sequentially with citric acid solution (17 mL of 15% aqueous solution), sodium bicarbonate solution (17 mL of saturated aqueous solution) and water (17 mL). The resulting solution was solvent switched to 2-propanol (17 mL) seeded and water (1.7 mL) was added. The solid was filtered and dried in vacuo to provide compound 7 (1.33 g, 75%).

Example 3

Alternative Preparation of Compound 7

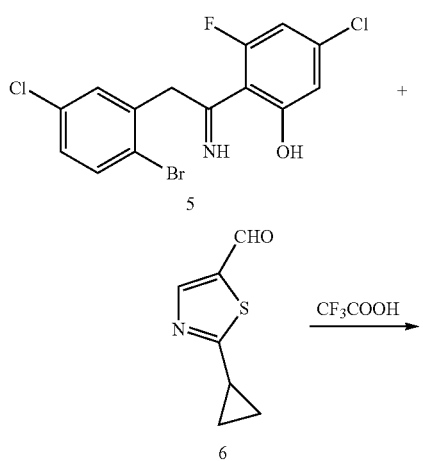

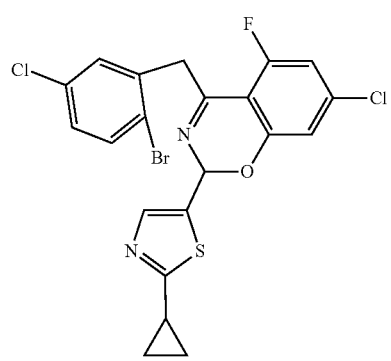

7

To a dry 1000 mL flask was charged activated 4 Å molecular sieves (55 g) followed by compound 5 (25 g, 66.3 mmol), 2-cyclopropylthiazole-5-carbaldehyde (20.32 g, 133 mmol) and DCM (275 mL). The resulting slurry was cooled using an ice-water bath then 2,2,2-trifluoroacetic acid (15.33 mL, 199 mmol) was added over 10 minutes while maintaining the reaction temperature below 10° C. The resulting reaction was allowed to stir at room temperature for about 20 hours, then was cooled using an ice-water bath, and triethylamine (28.8 mL, 206 mmol) was added to the cooled solution using a syringe pump (T batch<15° C.). The reaction mixture was then filtered to remove molecular sieves, and washed with DCM. The organic layer was washed sequentially with water (60 mL), citric acid (5% aq. 60 mL), brine (5% wt 100 mL), NaHCO$_3$ (2 wt %, 70 mL), brine (2 wt %, 70 mL), dried over MgSO$_4$, filtered and concentrated in vacuo. The resulting residue was taken up into 270 mL ethyl acetate at 45° C., then the solution was seeded and concentrated at 200 psi to about 3-4 volumes. Heptane (200 mL) was added over 2 hours and the resulting solution was cooled to 25° C. The solid formed was filtered and washed with ethyl acetate/Heptene=1/3 (2×40 mL) to provide a crude product that was recrystallized from ethyl acetate/heptane (1/2) to provide compound 7 (26 g) as a solid. 1H NMR (CDCl$_3$): δ 7.54 (s, 1H), 7.51 (d; J=8.5 Hz, 1H), 7.21 (d, J=2.5 Hz, 1H), 7.13 (dd, J=8.5, 2.5 Hz, 1H), 6.80 (d; J=1.8 Hz, 1H); 6.78 (dd, J=10.4, 1.8 Hz), 6.61 (s, 1H), 4.23 (d, J=8.4 Hz, 1H), 4.21 (d, J=8.2 Hz, 1H); 2.28-2.23 (m, 1H), 1.13-1.09 (m, 2H), 1.08-1.04 (m, 2H); 1H NMR (CDCl$_3$): 175.6, 160.6, 160.2 (d, J=6.1 Hz), 158.5, 156.2 (J=7.0 Hz), 141.8, 139.9 (d, J=13.9 Hz), 138.2 (d, J=2.0 Hz), 133.9, 133.3 (d, J=21.6 Hz), 131.3, 128.8, 123.5, 114.0 (d, J=6.3 Hz), 111.0 (d, J=7.3 Hz), 106.5 (d, J=16.4 Hz), 84.1, 43.9 (d, J=8.7 Hz), 14.8, 11.4 (d, J=4.1 Hz); [M+1]:512.8.

Example 4

Alternate Preparation of Compound 7 Using Imine Coupling Partner

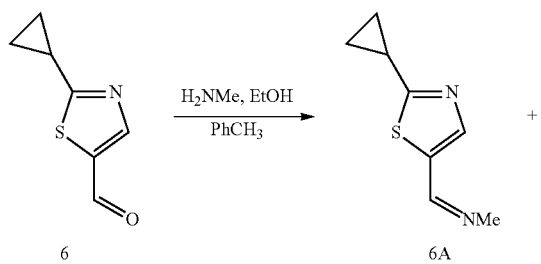

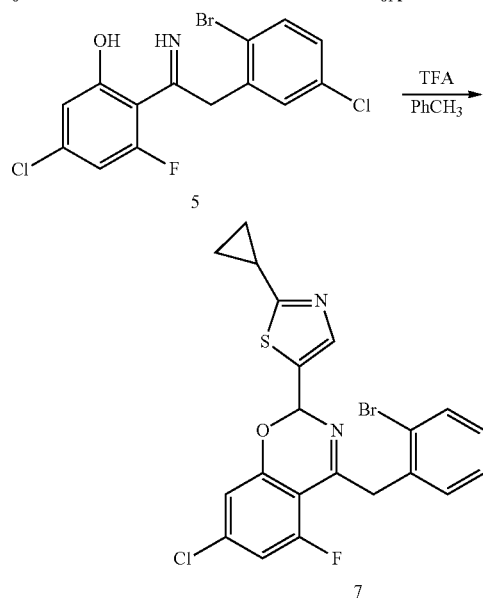

Step A: Synthesis of Compound 6A

A solution of methylamine in ethanol (33 wt %, 3.7 g, 39.2 mmol) was added to a solution of 2-cyclopropylthiazole-5-carbaldehyde (6, 2.0 g, 13.1 mmol) in toluene (15 mL) at room temperature. The resulting solution was allowed to stir at room temperature for 1.5 hours, then concentrated by removing 10 mL of solvent on rotary evaporator in vacuo. The resulting solution was diluted with Toluene, and concentrated in vacuo to a final volume of 12 mL on a rotary evaporator to provide a toluene solution of compound 6A (2.17 g, 13.1 mmol, 100% yield). $^1$H NMR (DMSO-d$_6$, 400 MHz): δ 8.42 (d, J=1.5 Hz, 1H), 7.88 (s, 1H), 3.36 (d, J=1.3 Hz, 3H), 2.41 (m, 1H), 1.14 (m, 2H), 1.00 (m, 2H)

Step B: Synthesis of Compound 7

The resulting solution of 6A obtained above was combined with a slurry of 2-(2-(2-bromo-5-chlorophenyl)-1-iminoethyl)-5-chloro-3-fluorophenol (5, 4.52 g, 12.0 mmol) in Toluene (90 mL). The resulting slurry was concentrated by removing 60 mL of solvent on a rotary evaporator, and the flask was then placed in a room temperature water bath. TFA (2.77 mL, 36.0 mmol) was added to The resulting solution over 5 minutes, and The resulting solution aged at room temperature for 18 hours. The resulting slurry was filtered, the flask and pad washed with Toluene (45 mL), and the Toluene filtrates combined. The resulting solution was washed sequentially with 4% wt/wt aq. NaHCO$_3$ (80 mL) and water (25 mL), then concentrated on a rotary evaporator. The resulting oil was concentrated twice from ethyl acetate (45 mL), leaving a residual solution of approximately 12 mL from which a solid precipitated. This slurry was warmed to a bath temperature of 50° C., then heptane (45 mL) was added over 1 hour. The resulting slurry was cooled to room temperature, aged for 15 hours, and cooled in an ice/water bath for 1 hour. The mixture was filtered, the flask and pad were washed with heptane (20 mL), and the solid was dried in vacuo at 50° C. to provide compound 7 (3.43 g, 56% yield).

Example 5

Alternate Preparation of Compound 7 Using Imine Coupling Partner

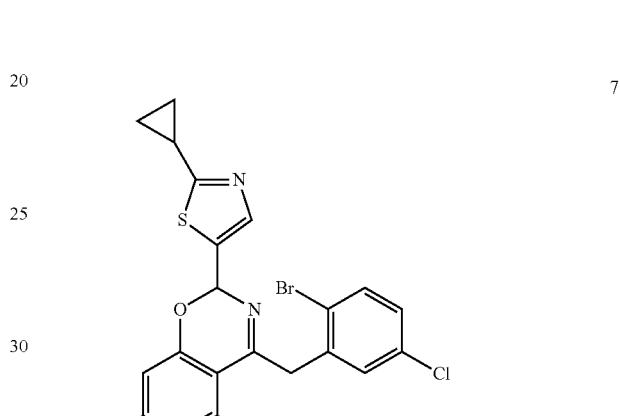

Step A: Synthesis of Compound 5a

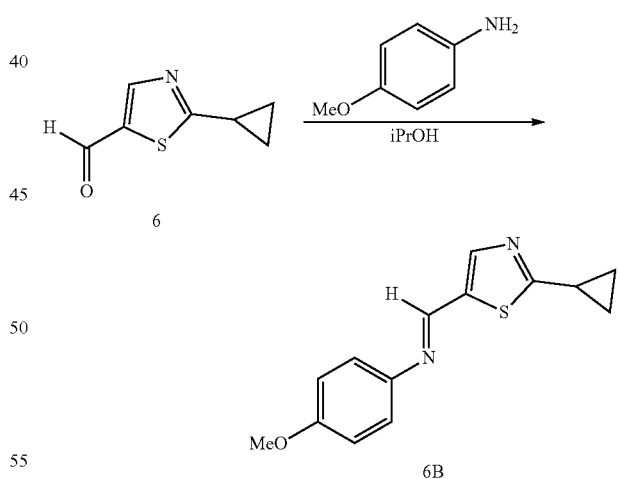

A 1 L round-bottom flask equipped with an air condenser was charged with compound 6 (25 g, 163 mmol), 4-methoxyaniline (22.1 g, 180 mmol), and isopropanol (250 mL). The resulting slurry was warmed to 50° C. and stirred for 3.5 hours, during which time a precipitate formed. The resulting slurry was cooled to 0° C., aged for 1 hour, and filtered. The flask and pad were rinsed twice with 0 isopropanol (84 mL), and the solid was dried to a constant weight in a vacuum oven at 50° C. to provide compound 6B (39.0 g, 93% yield). $^1$H NMR (DMSO-d$_6$, 400 MHz): δ 8.77 (s, 1H), 8.06 (s, 1H), 7.26 (d, J=8.8 Hz, 2H), 6.96 (d, J=8.8 Hz, 2H), 3.77 (s, 3H), 2.45 (m, 1H), 1.19 (m, 2H), 1.05 (m, 2H)—imine geometry not determined, drawn as (E) for convenience.

Step B: Synthesis of Compound 7 a constant weight in a vacuum oven at 50° C. to provide compound 7 (10.1 g, 74% yield).

Example 6

Preparation of Compound 8

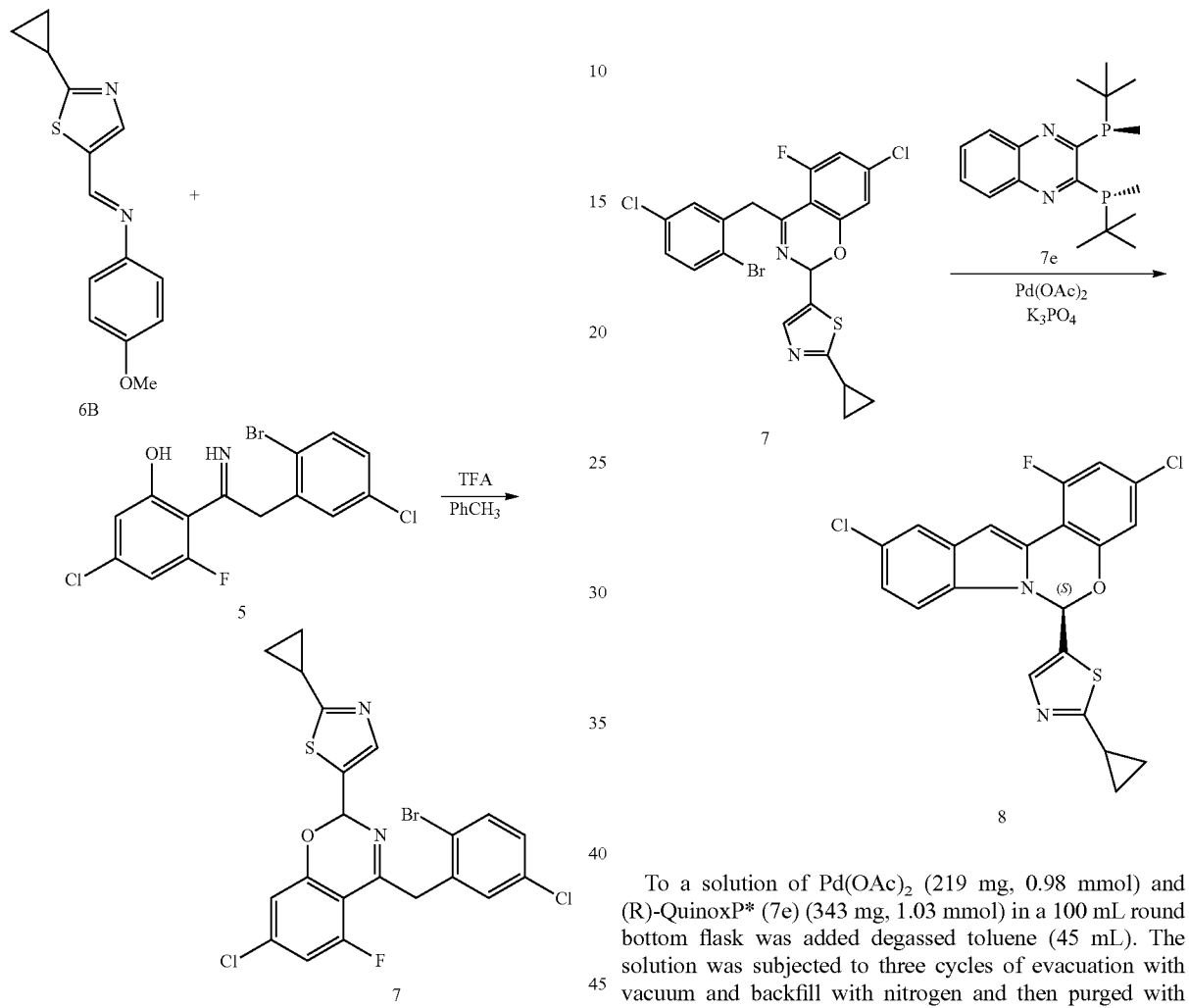

A 3-neck roundbottom flask equipped with a magnetic stirbar, a temperature probe, and a nitrogen inlet was charged with compound 6B (7.54 g, 29.2 mmol) and a solution of compound 5 in toluene (5.72 wt %, 174.8 g, 26.5 mmol) was added. The resulting suspension was allowed to stir at room temperature until the solid dissolved, and the resulting solution was cooled using an ice/water bath. TFA (2.45 mL, 31.8 mmol) was added while the internal temperature was maintained below 5° C. The resulting solution was allowed to stir in the ice/water bath for 16 hours as it warmed to room temperature. The resulting slurry was filtered, the flask and pad were washed with toluene (27 mL), and the organic solution was washed with aqueous NaHCO₃ (4 wt %, 54 mL) and water (54 mL). The organic layer was concentrated in vacuo to ~25 mL, diluted with isopropanol (110 mL), and concentrated in vacuo to ~50 mL total volume. The resulting slurry was warmed to 40° C., diluted with water (10 mL, added over 30 minutes), aged at 0° C. for 1 hour, and filtered. The flask and pad were washed with 4:1 isopropanol/water (25 mL), and the solid dried to To a solution of Pd(OAc)₂ (219 mg, 0.98 mmol) and (R)-QuinoxP* (7e) (343 mg, 1.03 mmol) in a 100 mL round bottom flask was added degassed toluene (45 mL). The solution was subjected to three cycles of evacuation with vacuum and backfill with nitrogen and then purged with nitrogen above surface for 5 minutes. The catalyst solution was then allowed to age at 20° C. for 2 hours. A 1 L, 3-neck round bottom flask fitted with an overhead stirrer was then charged with compound 7 (25 g, 48.8 mmol) and K₃PO₄ (41.4 g, 195 mmol) and toluene (700 mL). The mixture was subjected to three cycles of vacuum evacuation and nitrogen backfill and then purged with nitrogen above surface for 5 minutes. Degassed water (0.88 mL, 48.8 mmol) was then added dropwise, after which the premade catalyst solution was added and the resulting reaction was heated to 50-55° C. and allowed to stir at this temperature for 11 hours. During the first 6 hours of the reaction time, additional water (5.28 mL, 293 mmol) was added in six equal portions, each hour. After a total of 11 hours at 50-55° C., the reaction mixture was cooled to 20° C. and charged with 75 mL of water and 5 mL 50% w/v KOH (~9N). The aqueous layer was cut away and the organic layer was washed with 100 mL of water. The organic layer was then filtered and concentrated in vacuo and the resulting residue was purified using flash column chromatography to provide compound 8. The ee was determined using SFC under the following conditions:

Column: ChiralCel OJ-3; 4.6 mm×150 mm; 3 μm particle size
Temperature: 40° C.
Pressure: 200 bar
Modifier: IPA with 25 mM isobutyl amine added
Flowrate: 3.0 mL·min
Conditions: 1% modifier/99% CO2 to 40% modifier/60% CO$_2$ over 5 minutes with 1 minute hold at 40% modifier
For purified compound 8: (23 mg, 90% yield, in 91% ee). $^1$H NMR (CDCl3, 500 MHz): δ 7.663 (d, J=2.0 Hz, 1 H), 7.407 (d, J=0.4 Hz, 1H), 7.200 (dd, J=2.0, 8.8 Hz, 1H), 7.092 (d, J=0.4 8.4 Hz, 1H), 7.048-7.039 (m, 2H), 6.958-6.910 (m, 2H), 2.194-2.153 (m, 1H), 1.275-1.075 (m, 2H), 1.018-0.991 (m, 2H).

Example 7

Preparation of Compound 9

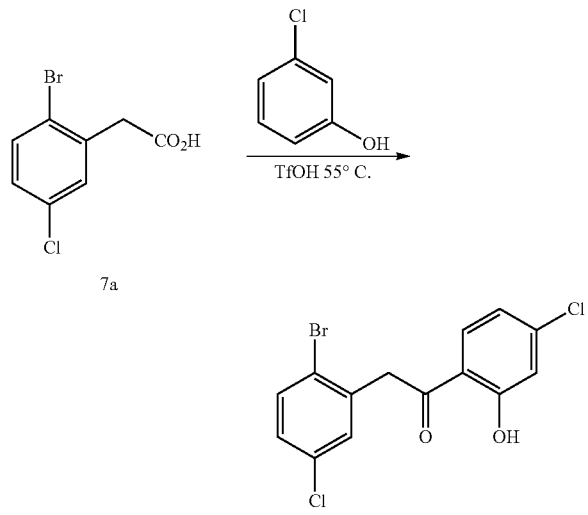

Step A: Synthesis of Compound 7b

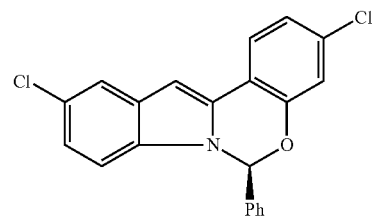

Into a 1000 mL flask was charged 2-(2-bromo-5-chlorophenyl) acetic acid (7a, 60 g, 242 mmol) and trifluoromethanesulfonic acid (1.1 kg). The mixture was allowed to stir for 10 minutes, then 3-chlorophenol (27 g, 211 mmol) was added. The reaction was heated to 55 degrees and allowed to stir at this temperature for about 15 hours. The reaction mixture was then cooled to room temperature and poured into 3 kg of ice-water. The suspension formed was allowed to stir for 30 minutes and then filtered. The solid was collected and washed with water (300 mL×3). The solid was dissolved in ethyl acetate (1000 mL was discard) and the collected organic layer was dried with Na$_2$SO$_4$, filtered and concentrated in vacuo to provide compound 7b (82 g, crude) as a solid. It was used directly to the next step. $^1$H NMR (500 MHz, CDCl$_3$): δ (ppm) 12.10 (s, 1H), 7.81 (d, 1H, J=8.5 Hz), 7.55 (d, 1H, J=8.5 Hz), 7.26 (d, 1H, J=3.5 Hz), 7.20 (dd, 1H, J=8.5 Hz, 2.5 Hz), 7.05 (d, 1H, J=2.5 Hz), 6.95 (dd, 1H, J=8.5 Hz, 2.0 Hz), 4.42 (s, 2H). $^{13}$C NMR (125 MHz, CDCl$_3$): δ (ppm) 200.8, 163.3, 142.7, 135.6, 133.9, 133.6, 131.6, 130.8, 129.3, 122.9, 119.9, 118.8, 117.6, 45.2. HRMS TOF MS (m/z): [M+H]$^+$ calcd for [C$_{14}$H$_9$BrCl$_2$O$_2$H] 358.9241; found 358.9240. FTIR(neat): 3074 (br), 1627, 1605, 1567, 1461, 1410, 1352, 1260 cm$^{-1}$.

Step B—Synthesis of Compound 7c

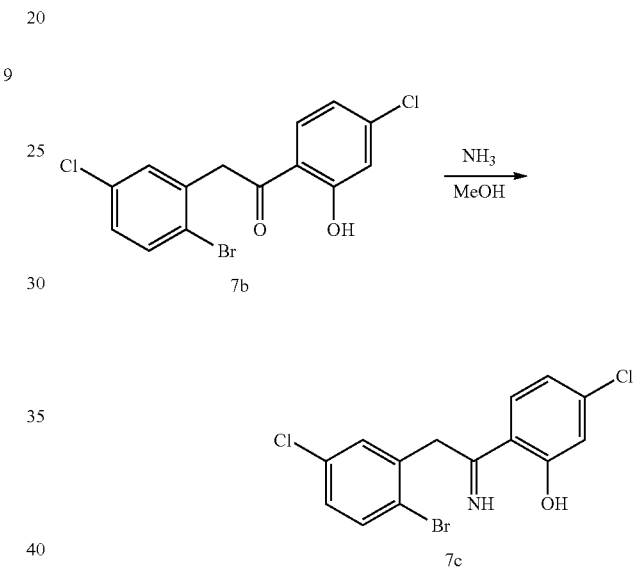

A solution of ammonia (7 M in methanol) was added to compound 7b (10 g) and the resulting reaction was allowed to stir at room temperature for 20 hours. The slurry formed was filtered and the collected solid was washed with methanol then dried in vacuo to provide compound 7c as a solid 8.6 g, 86% yield.

Step C: Synthesis of Racemic Compound 7d

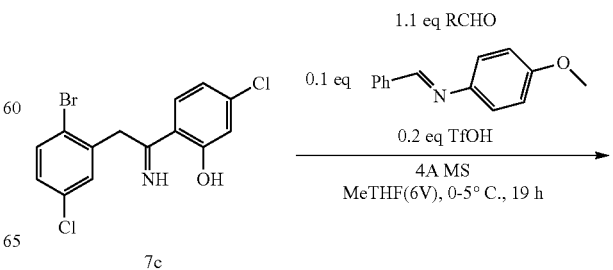

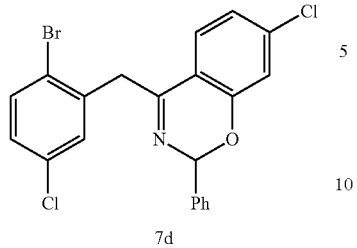

7d 3 g of 4 A molecular sieves (60 wt/wt %) is suspended in 2-Methyl-THF (300 mL) under nitrogen atmosphere and cooled to 0° C., stirred for 10 min. 2-(2-(2-bromo-5-chlorophenyl)-1-iminoethyl)-5-chlorophenol (5 g, 13.9 mmol), aldehyde (15.3 mmol) and imine (1.39 mmol) is added, stirred for 2 minutes while maintaining reaction temperature at 0-5° C. Trifluoromethanesulfonic acid (0.418 g, 2.79 mmol) was added dropwise over 1 minute, then the mixture was warmed to room temperature and allowed to stir at this temperature for about 15 hours. The reaction mixture was filtered and the collected sieves were washed with 2-MeTHF (5 mL). The organic phase was then washed sequentially with 5 wt % NaHCO$_3$ solution (25 mL), then water (25 mL). The organic phase was collected and concentrated in vacuo. The resulting residue was purified via crystallization from MeOH (25 mL) to provide 4-(2-bromo-5-chlorobenzyl)-7-chloro-2-phenyl-2H-benzo[e][1,3]oxazine (1a) as a solid (82% yield). $^1$H NMR (500 MHz, CDCl$_3$): δ (ppm) 7.55-7.52 (m, 3H), 7.42-7.34 (m, 3H), 7.30 (d, 1H, J=3.5 Hz,) 7.29 (s, 1H), 7.13-7.10 (dd, 1H, J=8.5 Hz, 2.5 Hz), 6.95-6.91 (m, 2H), 6.57 (1H, s), 4.16 (ABq, 2H, J=16.5 Hz). $^{13}$C NMR (125 MHz, CDCl$_3$): δ (ppm) 161.5, 155.8, 139.2, 138.9, 138.1, 133.8, 133.5, 130.6, 128.8, 128.7, 128.5, 127.0, 126.3, 122.6, 121.9, 117.3, 116.2, 88.9, 40.8. HRMS TOF MS (m/z): [M+H]$^+$ calcd for [C$_{21}$H$_{14}$BrCl$_2$NOH] 445.9709; found 445.9713. FTIR(neat): 3060, 1633, 1596, 1454, 1364, 1344 cm$^{-1}$.

Step E: Synthesis of Compound 9

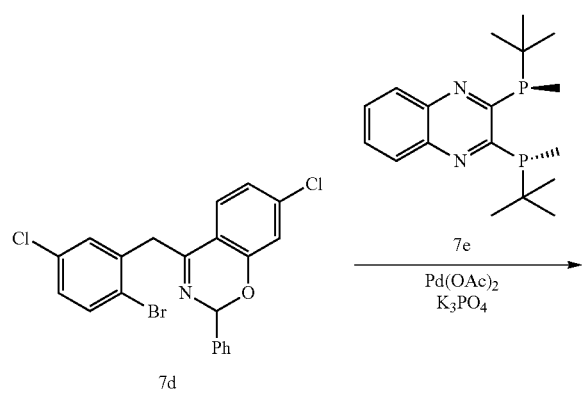

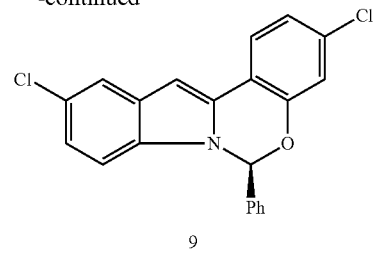

9

In a glove box, a solution of compound 7e (commercially available, 2.47 mg, 0.0074 mmol, 2.2%) and diacetoxypalladium (1.51 mg, 0.0067 mmol, 2% cat.) in toluene (200 uL) was heated at 40° C. for 2 hours. The resulting solution was then transferred into a mixture of compound 7d (15 mg, 0.034 mmol) and K$_3$PO$_4$ (53 mg, 0.252 mmol) in toluene (0.75 mL). The resulting reaction was heated at 60° C. for 15 hours. Then the mixture was cooled, filtered and concentrated in vacuo. The resulting residue was then purified using preparative TLC to provide compound 9. The ee was determined using SFC under the following conditions:

Column: ChiralPak IC-3; 4.6 mm×150 mm; 3 μm particle size

Temperature: 40° C.

Pressure: 200 bar

Modifier: MeOH

Flowrate: 3.0 mL·min

Conditions: 1% modifier/99% CO2 to 40% modifier/60% CO2 over 5 minutes with 1 minute hold at 40% modifier Compound 9: (~11 mg, 99% yield, in 95% ee). $^1$H NMR (CDCl3, 400 MHz): δ 7.64 (d, J=2.0 Hz, 1 H), 7.62-7.60 (m, 1 H), 7.37-7.30 (m, 3 H), 7.14 (s, 1 H), 7.13-7.10 (m, 2 H), 7.07 (t, J=1.9 Hz, 1 H), 7.06-7.05 (m, 2 H), 6.86 (s, 1 H), 6.76 (d, J=8.8 Hz, 1 H).

Example 8

Preparation of Compound 10

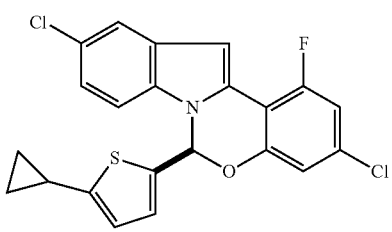

10

Step A: Synthesis of Compound 8b

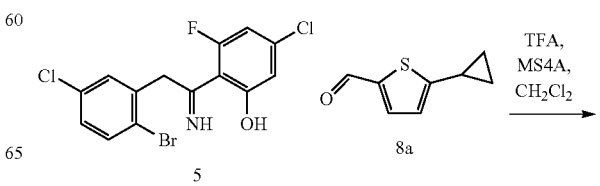

-continued

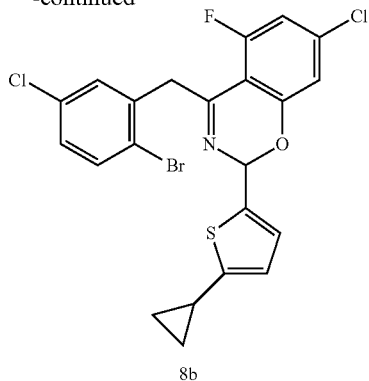

8b

In a dry 100 mL RB flask was placed powdered molecular sieves (4 Å, 3.3 g). The flask was evacuated and heated with a heat gun in vacuo. After cooling to room temperature, dichloromethane (15 mL) was added. To the resulting solution was added Compound 8a (0.81 g) and compound 5 (1.0 g). To the resulting reaction was added trifluoroacetic acid (0.41 mL) and the reaction was allowed to stir at room temperature for about 15 hours. Additional trifluoroacetic acid (0.20 mL) was added and the reaction was allowed to stir for an additional 6 hours, then was quenched using triethylamine (1.85 mL). The resulting mixture was filtered, and concentrated in vacuo. The residue obtained was purified using flash column chromatography to provide 0.22 g of compound 8b. LRMS=512 (M+H).

Step B: Synthesis of Compound 10

In the glove box, a resulting solution of compound 7e (4.68 mg, 0.014 mmol, 2.2%) and diacetoxypalladium (2.86 mg, 0.013 mmol, 2% cat.) in toluene (400 uL) was heated at 40° C. for 2 hours. Then The resulting solution was transferred into a mixture of compound 8b (30 mg, 0.064 mmol) and $K_3PO_4$ (101 mg, 0.48 mmol) in toluene (1.0 mL). The resulting mixture was heated at 60° C. for 15 hours. Then the mixture was cooled and filtered. The reaction mixture was filtered and concentrated in vacuo. The residue obtained was purified using silica-gel column chromatography to provide compound 10. The ee was determined using SFC under the following conditions:

Column: ChiralCel OJ-3; 4.6 mm×150 mm; 3 µm particle size
Temperature: 40° C.
Pressure: 200 bar
Modifier: IPA with 25 mM isobutyl amine
Flowrate: 3.0 mL·min
Conditions: 1% modifier/99% CO2 to 40% modifier/60% $CO_2$ over 5 minutes with 1 minute hold at 40% modifier For purified compound 10: (18 mg, 85.6%, 86% ee). $^1$H NMR (CDCl3, 400 MHz, ppm): 7.65 (d, J=1.8 Hz, 1 H), 7.31 (s, 1 H), 7.16 (dd, J=2.0, 8.8 Hz, 1 H), 7.03-7.01 (m, 2 H), 6.92-6.89 (m, 2 H), 6.48 (d, J=3.6 Hz, 1 H), 6.36 (d, J=3.5 Hz, 1 H), 2.00-1.93 (m, 1 H), 0.98-0.93 (m, 2 H), 0.68-0.64 (m, 2 H).

Example 9

Preparation of Compound 12

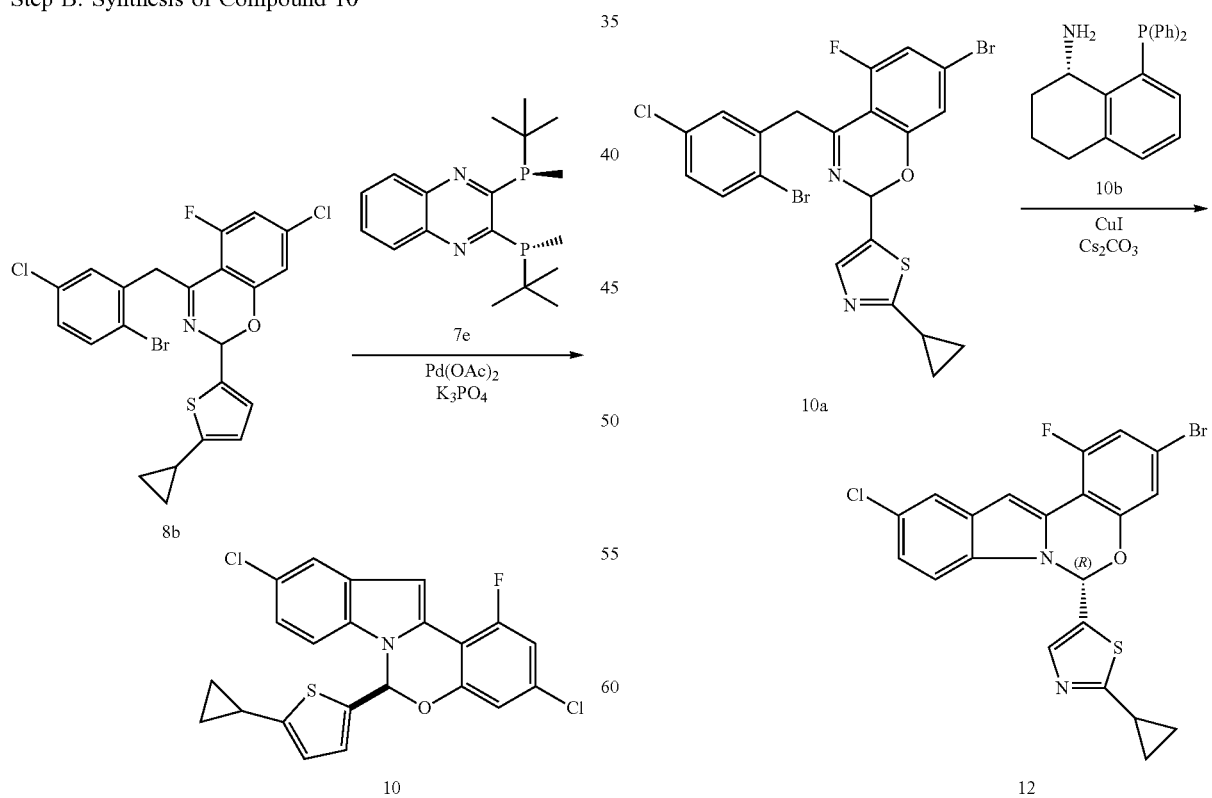

In a glove box, a solution of copper(I) iodide (0.076 mg, 0.0004 mmol, 10% cat.) in acetonitrile (50 μL) was added to compound 10b (commercially available, 0.14 mg, 0.000422 mmol, 11%) and heated to about 55° C. for about 2 h. The solvent was then removed in vacuo and Cs₂CO₃ (9.8 mg, 0.030 mmol) was added. Compound 10a (prepared using the methods described above to make compound 7 and substituting the appropriate reactants, 2.3 mg, 0.004 mmol) was then added as a solution in 2-methyltetrahydrofuran (0.1 mL) and the resulting mixture heated to about 65° C. for 24 h to provide compound 12 in 68% ee.

Example 10

Preparation of Compound 13

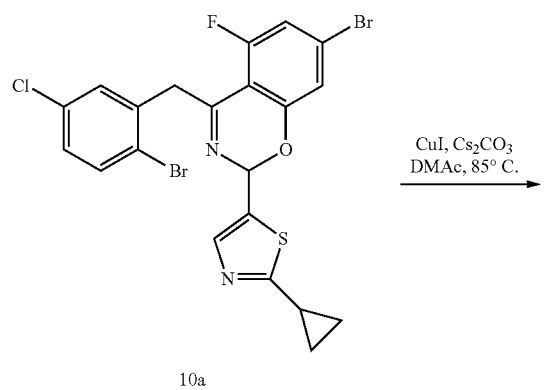

In a glove box, a suspension of compound 10a (16 mg), CuI (1.37 mg, 0.25 eq.) and Cs₂CO₃ (28 mg, 3 eq.) in DMAc (0.5 mL) was heated to 85° C. and allowed to stand at this temperature for 18 hours. The reaction mixture was then diluted with ethyl acetate (10 mL) and washed with water (2×5 mL). The organic layer was dried over Na₂SO₄, filtered and concentrated in vacuo. The resulting residue was purified using flash column chromatography to provide compound 13 (racemic, 8 mg, 60% yield). ¹H NMR (CDCl3, 500 MHz): δ 7.67 (d, J=2.0 Hz, 1 H), 7.42 (s, 1H), 7.21 (dd, J=2.0, 8.5 Hz, 1H), 7.06-7.12 (m, 5 H), 2.19-2.16 (m, 1H), 1.08-1.12 (m, 2H), 1.00-1.03 (m, 2H).

Example 11

Preparation of CSA Salt of Compound 8

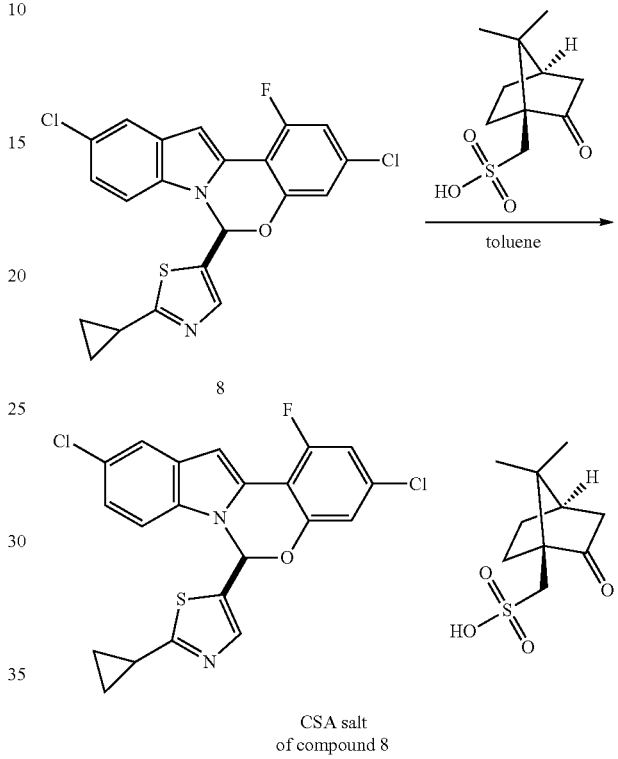

The crude product of compound 8, obtained using the method described in Example 6 (21 g theoretic yield, 48.8 mmol) was dissolved in ~50 mL of toluene and 128 mL of iPAC at 45° C. (S)-Camphorsulfonic acid (10.8 g, 46.4 mmol) was added over 2.5 hours in three portions at 45° C. It was cooled to room temperature and additional (S)-camphorsulfonic acid (0.57 g, 2.4 mmol) was added. After aging at room temperature for 16 hrs, the mixture was filtered. The solid was washed with 50 ml 1/2.5 toluene/isopropyl acetate and then 50 ml isopropyl acetate, and dried with vacuum to afford 27.1 g of 8 (40.8 mmol) as its camphorsulfonic acid (CSA) salt in 96 to >99% ee.

Example 12

Preparation of Ligand 13 b

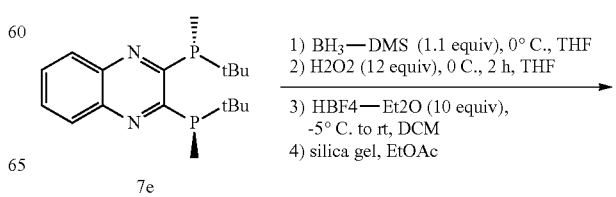

-continued

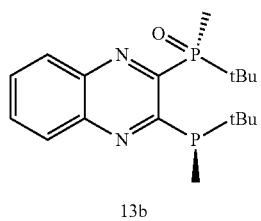

13b (R)-QuinoxP* (compound 7e, commercially available, 0.454 g, 1.358 mmol, 1.0 equiv) was taken up in dry tetrahydrofuran (13.5 mL) at room temperature. The resulting solution was cooled to 0° C. and BH$_3$—SMe$_2$ (0.14 mL, 1.494 mmol, 1.1 equiv) was added in one portion. The resulting reaction was allowed to stir at 0° C. for 40 minutes and aqueous 35 wt % H$_2$O$_2$ (1.4 mL, 16.3 mmol, 12 equiv) was added over 5 minutes. The resulting solution was allowed to stir at 0° C. for 2 hours and was then quenched by the addition of saturated aqueous Na$_2$SO$_3$ (20 mL). The mixture was then diluted with ethyl acetate (20 mL). The layers were separated and the aqueous layer was washed twice with 20 mL of ethyl acetate. The combined organic layers were dried over Na$_2$SO$_4$ and filtered. The filtrate was concentrated in vacuo to dryness and dried further at room temperature in vacuo with nitrogen purge for 16 hours. The residue obtained was taken up in dichloromethane (13.5 mL) and cooled to −5° C. HBF$_4$-etherate (1.85 mL, 13.58 mL, 10 equiv) was added in one portion. Vigorous gas evolution was observed during the acid addition. The cooling bath was removed and the resulting solution was allowed to stir at room temperature for 1 hour. The mixture was quenched with 40 mL of saturated aqueous KHCO$_3$ which had been degassed with nitrogen. The biphasic mixture was diluted with 30 mL of MTBE and the layers were separated. The aqueous layers were washed twice with 30 mL of MTBE. The combined organic layers were dried over Na$_2$SO$_4$ and filtered. The filtrate was concentrated in vacuo to dryness and the residue obtained was purified using flash column chromatography on silica gel chromatography (50% ethyl acetate/hexanes to 100% ethyl acetate) to provide (R)-QuinoxP* monoxide (13b, 320 mg, 67%) as a solid. $^1$H NMR (400 Mhz, CDCl3) δ 8.165 (dd, J=1.28, 8.36 Hz, 1H), 8.069 (dd, J=1.52, 8.17 Hz, 1H), 7.817 (m, 2H), 1.977 (d, J=12.8 Hz, 3H), 1.459 (d, J=6.9 Hz, 3H), 1.186 (d, J=13.7 Hz, 9H), 1.088 (d, J=11.8 Hz, 9H); $^{31}$P NMR (162 Mhz, CDCl3) δ 51.16 (d, J=4.1 Hz), −11.9 (d, J=3.8 Hz); LRMS calcd. for C$_{18}$H$_{29}$N$_2$OP$_{32}$ [M+H]$^+$ 351; found 351.

Example 13

Preparation of Intermediate Compound 14g

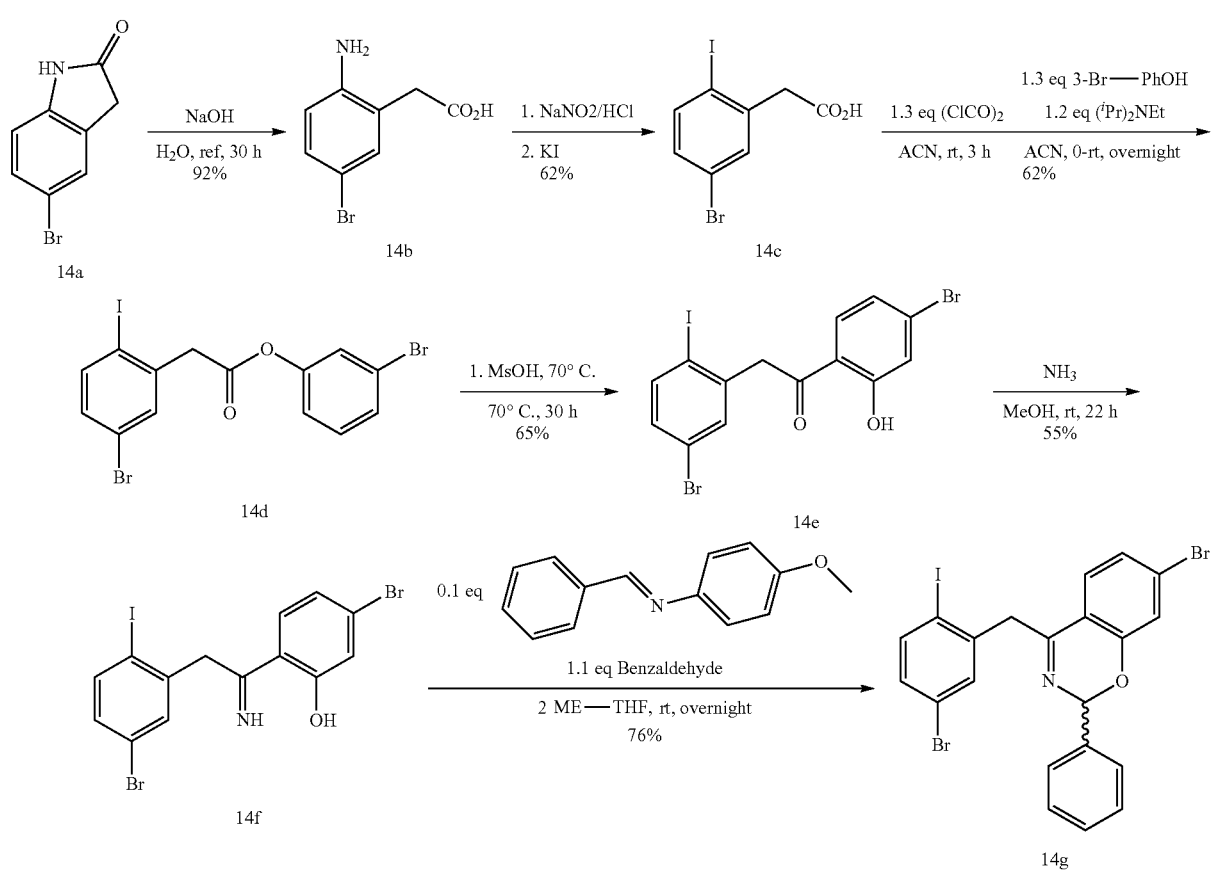

Step A—Synthesis of Compound 14b

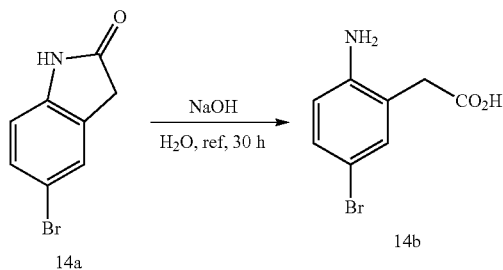

A 3000-mL 3-necked round-bottom flask was purged and maintained with an inert atmosphere of nitrogen. 5-Bro
Step B—Synthesis of Compound 14c

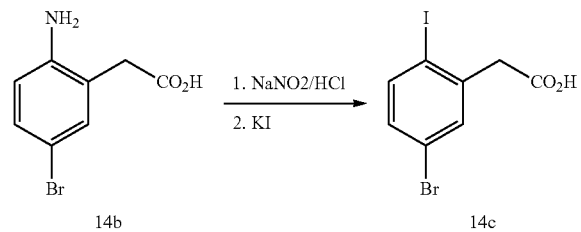 [SMILES: Nc1ccc(Br)cc1CC(=O)O ; O=C(O)Cc1cc(Br)ccc1I]

Into a 5-L flask was charged hydrochloric acid, 37% (1000 ml) and water (1000 mL). 2-(2-Amino-5-bromophenyl)acetic acid (230 g, 871 mmol) was added batchwise at r.t in 20 minutes. The suspension was allowed to stir for 1 hour, and then cooled to −5° C. A solution of sodium nitrite (66.1 g, 958 mmol) in 100 mL water was added dropwise at −5 to 0° C. over 2.5 hours. The mixture was allowed to stir for further 1 h at −5 to 0° C. The solution was labelled as solution A.

Into a 5000 mL flask was charged water (1000 mL) and potassium iodide (795 g, 4.79 mmol). The solution was heated to 50° C. Solution A was added dropwise over 2 hours. The resulting solution was allowed to stir for a further 2 hours at 50° C. LCMS showed reaction completed conversion. The cake was dried in vacuo to obtain compound 14c (210 g, 616 mmol, 61.6% yield) as a solid.

Step C—Synthesis of Compound 14d

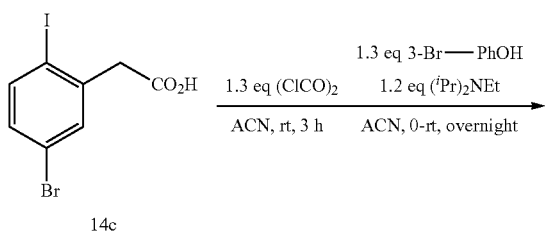

Into a 5000 mL flask was charged 2-(5-bromo-2-iodophenyl)acetic acid (190 g, 557 mmol) and acetonitrile (1900.0 mL). Oxalyl dichloride (91.9 g, 724 mmol) was added dropwise room temperature, then stirred for 1 hour at room temperature. The mixture was concentrated in vacuo to provide an oily residue which was taken up in acetonitrile (1900.0 mL). To the resulting solution was added 3-bromophenol (92 g, 724 mmol) and diisopropylethylamine (94 g, 724 mmol)—dropwise at −10° C. The resulting reaction was allowed to stir for about 15 hours at room temperature. The solvent was removed by distillation in vacuo. The residue obtained was purified using flash column chromatography on silica gel column (eluent: ethyl acetate/petroleum ether (1:100)) to provide compound 14d (170 g, 276 mmol, 61.6% yield) as a solid.

Step D—Synthesis of Compound 14e

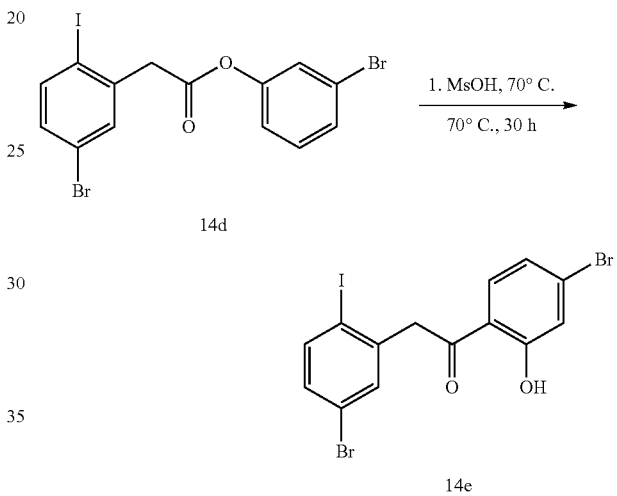

In a 2000 mL flask, methanesulfonic anhydride (76 g, 5.74 mmol) and methanesulfonic acid (1900 g, 104 mmol) were placed. The resulting solution was heated at 90° C. for 2 hours. The solution was cooled to 70° C., and 3-bromophenyl 2-(5-bromo-2-iodophenyl)acetate (170 g, 276 mmol) was added. The resulting solution was heated at 70° C. for 30 hours. After cooling to room temperature, the mixture was diluted with water (1000 mL) and the resultant slurry of product was filtered. The product cake was slurry washed with water, 15% aqueous sodium carbonate solution and then MeOH:water (1:1). The washed cake was then dried in vacuo to provide compound 14e (110 g, 222 mmol, 65% yield)

Step E—Synthesis of Compound 14f

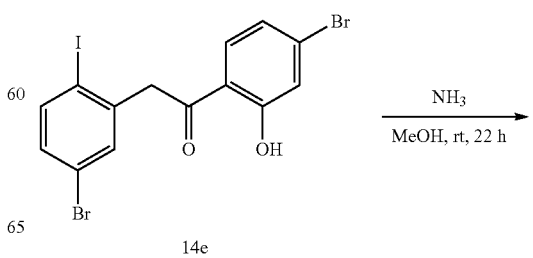

43

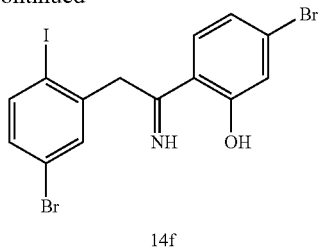

14f

A solution of ammonia (1000 mL, 9 M in MeOH) was added to 1-(4-bromo-2-hydroxyphenyl)-2-(5-bromo-2-iodophenyl)ethanone (110 g, 222 mmol) and the mixture was allowed to stir at room temperature for 20 h. The resulting slurry was filtered and the product cake was washed with MeOH. After vacuum drying, compound 14f (60 g, 121 mmol, 55% yield) was obtained as a solid.

Step F—Synthesis of Compound 14g

44

0.404 mmol), benzaldehyde (14 g, 0.444 mmol), (E)-N-benzylidene-4-methoxyaniline (1.6 g, 0.040 mmol) was added. After the solution was allowed to stir for 5 min, trifluoromethanesulfonic acid (3.636 g, 0.081 mmol) was added. The resulting solution was allowed to stir for about 15 hours at room temperature. The reaction was quenched by the addition of 200 ml of NaHCO3 solution. The organic layer was separated and the aqueous was re-extracted with ethyl acetate (1×200 mL). The combined organic fractions were washed with brine (1×300 mL), dried with Na2SO4, filtered and the filtrate was evaporated in vacuo. The residue obtained was recrystallized from methanol. The solid was collected and dried in vacuo at room temperature to provide compound 14g (53.5 g, 0.343 mmol, 76% yield) as a solid. LC-MS (ES, m/z): (M+1)=582, 584, 586. H-NMR (400 MHz, CDCl$_3$) δ 7.68 (d, J=8.42 Hz, 1H), 7.54-7.47 (m, 2H),

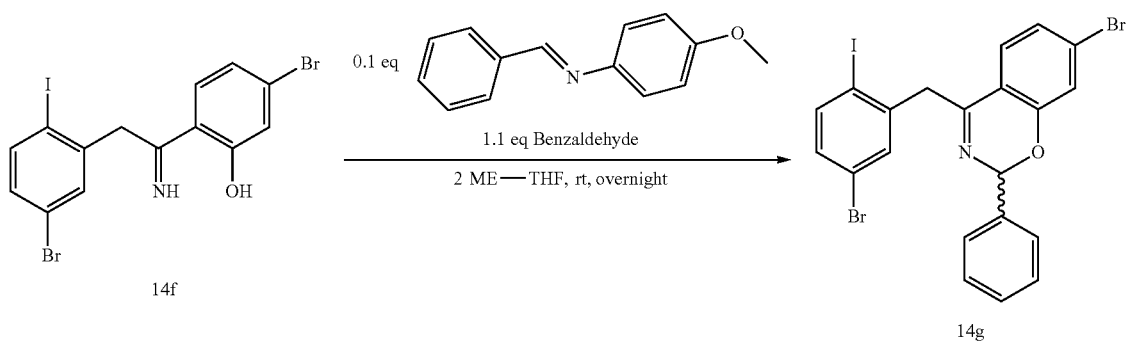

Into a 1000 ml 4-neck round-bottom flask purged and maintained with an inert atmosphere of nitrogen, was placed 4 A molecular sieves (30 g) and 2-Methyl-THF (420 ml), the suspension was allowed to stir for 10 minutes. 5-bromo-2-(2-(5-bromo-2-iodophenyl)-1-iminoethyl)phenol (60 g, 7.42-7.28 (m, 4H), 7.17 (d, J=8.26 Hz, 1H), 7.13-7.02 (m, 3H), 6.55 (s, 1H), 4.21-4.06 (m, 2H).

Example 14

Preparation of Intermediate Compound 15g

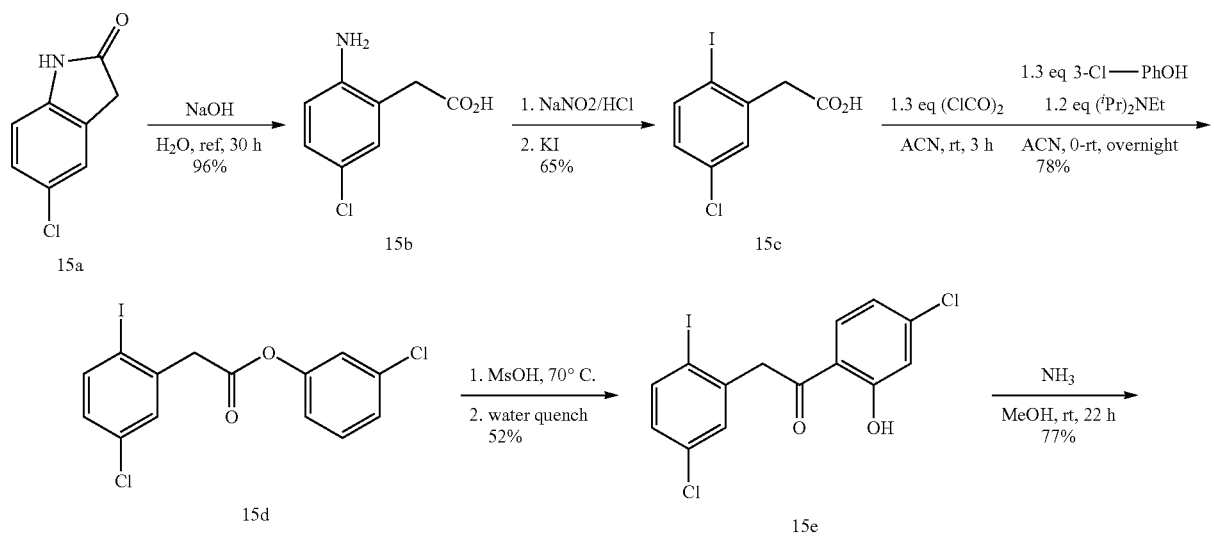

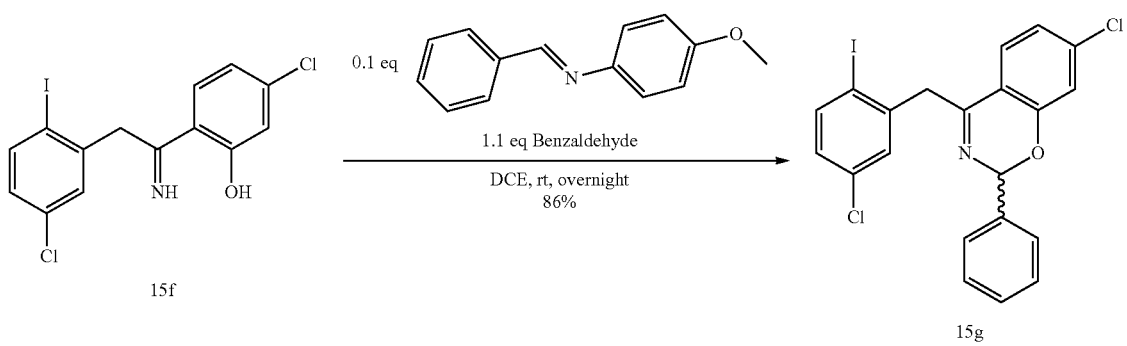

Step A—Synthesis of Compound 15b

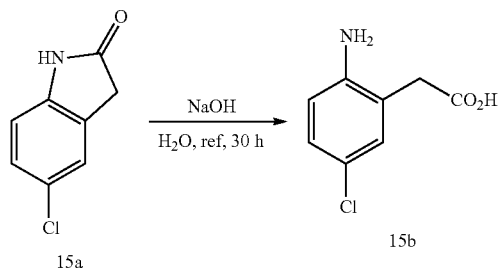

A 3000-mL 4-necked round-bottom flask was purged and maintained with an inert atmosphere of nitrogen. 5-Chloroindolin-2-one (15a, 160 g, 952 mmol) and sodium hydroxide (1193 mL, 4773 mmol) were added. The resulting solution was allowed to stir for 30 h at 100° C. The pH value of the solution was adjusted to 6 with hydrogen chloride (6 mol/L). The solid was collected by filtration to provide compound 15b (170 g, 916 mmol, 96% yield).

Step B—Synthesis of Compound 15c

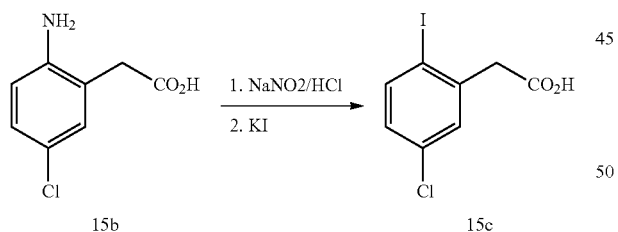

Into a 5-L flask was charged hydrochloric acid, 37% (850 mL) and water (1000 mL) Compound 15b (170 g, 916 mmol) was added batchwise at room temperature in 20 minutes. The suspension was allowed to stir for 1 hour, and then cooled to −5° C. A solution of sodium nitrite (76 g, 1099 mmol) in 200 mL water was added dropwise at −5 to 0° C. over 2.5 hours. The mixture was allowed to stir for further 1 h at −5 to 0° C. The solution was labelled as solution A.

Into a 10 L flask was charged water (850 mL), con.sulfuric acid (90 g, 916 mmol) and potassium iodide (243 g, 1465 mmol). The solution was heated to 50° C. Solution A was added dropwise for 2 hours. The resulting solution was allowed to stir for a further 2 hours at 50° C. LCMS showed complete conversion. The reaction mixture was poured into 3 L of ice-water and extracted with ethyl acetate (3000 mL*2). The combined organic layers were washed with Na2S2O3 and dried with Na2SO4, filtered and concentrated in vacuo to provide compound 15c (176 g, 594 mmol, 64.8% yield) as a solid.

Step C—Synthesis of Compound 15d

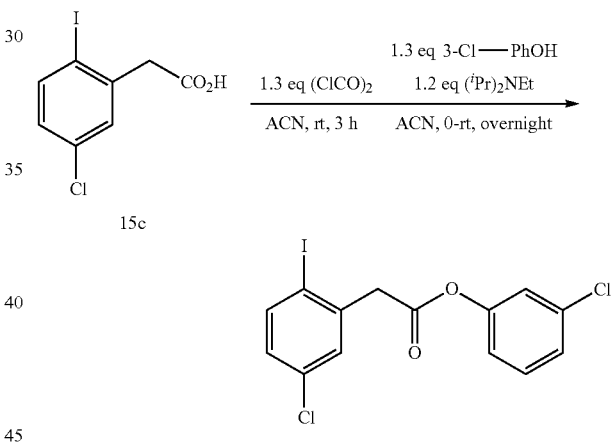

Into a 3 L flask was charged compound 15c (140 g, 472 mmol) and acetonitrile (1400 mL). Oxalyl dichloride (78 g, 614 mmol) was added dropwise at room temperature over 30 min. The solution was allowed to stir for 10 min at room temperature. LCMS showed complete conversion. 3-Chlorophenol (79 g, 614 mmol) was added a −10° C. over 5 min, diisopropylethylamine (73.8 g, 571 mmol) was added dropwise at −10° C. over 30 min. The solution was stirred for a further 30 min at −10° C. LCMS showed complete conversion. A mixture of ethyl acetate/H2O (1000 mL/1000 mL) was added and the resulting solution was allowed to stir for an additional 30 minutes. Organic layer was separated, aqueous layer was re-extracted with ethyl acetate (500 mL×2). The combined organic layers were dried with Na2SO4, filtered and concentrated in vacuo to provide crude product, which was purified on silica gel eluting with PE, to provide compound 15d (150 g, 369 mmol, 78% yield) as a solid.

Step D—Synthesis of Compound 15e

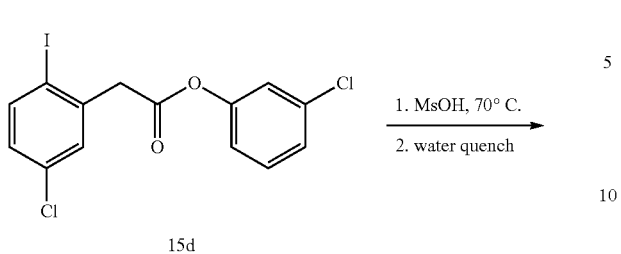

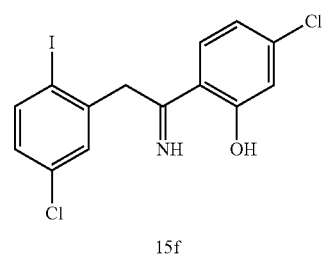

A solution of ammonia (7 M in MeOH) was added to compound 15e (50 g, 123 mmol) and the mixture was allowed to stir at room temperature for 20 hours. The resulting slurry was filtered and the product cake was washed with MeOH (100 mL×2). After vacuum drying, compound 15f was obtained as a solid (35 g, 94 mmol, 77% yield).

Step F—Synthesis of Compound 15g

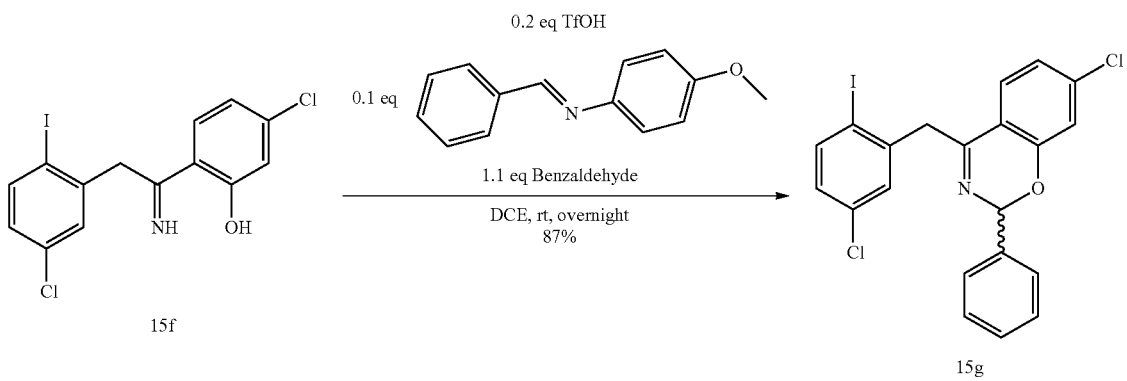 [SMILES: N=C(Cc1cc(Cl)ccc1I)c1ccc(Cl)cc1O ; COc1ccc(/N=C/c2ccccc2)cc1 ; Clc1ccc(I)c(CC2=NC(c3ccccc3)Oc3cc(Cl)ccc32)c1]

Dry methanesulfonic acid (750 g, 7804 mmol) was added to compound 15d (100 g, 246 mmol) and the resulting solution was heated at 70° C. for about 15 hours. After cooling to room temperature, the mixture was diluted with water (1000 mL). The mixture was extracted with ethyl acetate (500 mL×2). The combined organic layers were washed with water (500 mL×2) and brine (200 mL×1), dried with Na$_2$SO$_4$, filtered and concentrated in vacuo to provide crude product, which was purified using flash column chromatography on silica gel eluting with petroleum ether to provide compound 15e (52 g, 128 mmol, 52.0% yield) as a solid.

Step E—Synthesis of Compound 15f

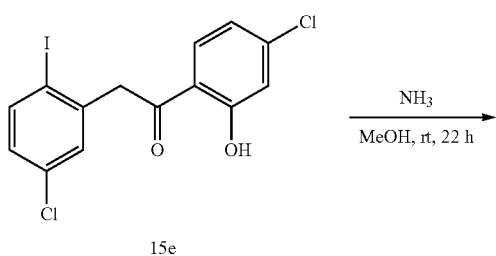

Into a 500 ml flask was charged 4 Å molecular sieves (18 g) and isopropyl acetate (245 mL). The solution was allowed to stir for 2 hour at 20° C. Compound 15f (35 g, 86 mmol), (E)-N-benzylidene-4-methoxyaniline (1.821 g, 8.62 mmol) and benzaldehyde (10.06 g, 95 mmol) were added at room temperature. After 10 min, trifluoromethanesulfonic acid (2.59 g, 17.24 mmol) was added. The mixture was allowed to stir at room temperature for 15 h. LCMS showed complete conversion. 5% NaHCO$_3$ (500 ml) was added and stirred for other 30 minutes. The organic layer was separated and the aqueous layer was re-extracted with ethyl acetate (200 mL×1). The combined organic layers were dried with Na2SO4, filtered and concentrated in vacuo. The solid obtained was suspended in MeOH (100 mL) and stirred for a further 1 hour. The resulting slurry was filtered and the collected solid was washed with MeOH (100 mL×2), then dried in vacuo to provide compound 15g (36.5 g, 73.9 mmol, 86% yield) as a solid. LC-MS: (ES, m/z): 494 [M+H]$^+$ H-NMR: (400 MHz, CDCl3, ppm): δ 7.80 (1H, d), 7.55 (2H, d), 7.47-7.37 (3H, m), 7.31-7.20 (2H, m), 7.05-6.98 (3H, m), 6.65 (1H, s), 4.23 (2H, s).

Example 15

Preparation of Ligands 16c and 16f

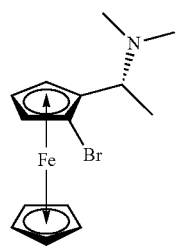

16a

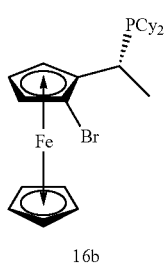

16b

Step A—Synthesis of Compound 16b

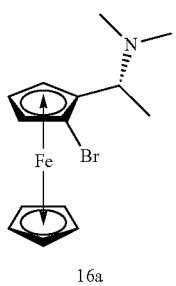 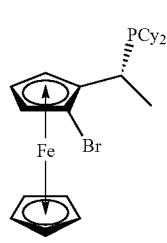

16a                16b

Into a 50-mL 3-necked round-bottom flask purged and maintained with an inert atmosphere of nitrogen, was placed [3-bromo-4-[(1R)-1-(dimethylamino)ethyl]cyclopenta-2,4-dien-1-yl](cyclopenta-2,4-dien-1-yl)iron (Compound 16a, 5 g, 14.88 mmol, 1.00 equiv), acetic acid (10 mL), and dicyclohexylphosphane (3.3 g, 16.64 mmol, 1.10 equiv). The resulting solution was heated to reflux for 2 hours, then cooled to room temperature and concentrated in vacuo and diluted with acetonitrile. The resulting solution was filtered and the collected solid dried in vacuo to provide 4.7 g (65%) of compound 16b as a solid.

Step B—Synthesis of Compound 16c

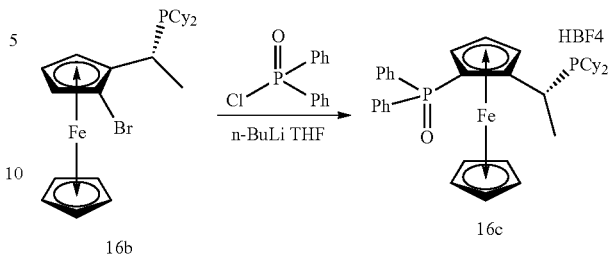

Into a 50-mL 3-necked round-bottom flask purged and maintained with an inert atmosphere of nitrogen, was placed compound 16b (1 g, 2.04 mmol, 1.00 equiv), tetrahydrofuran (10 mL). This was followed by the addition of butyllithium (200 mg, 3.12 mmol, 1.50 equiv) dropwise with stirring at −60° C. To this was added diphenylphosphinoyl chloride (730 mg, 3.08 mmol, 1.50 equiv) dropwise with stirring at −60° C. The reaction was allowed to stir for 2 hours at −60° C., then 40% $HBF_4$ solution (2.2 g, 5.00 equiv) was added. The resulting solution was allowed to stir for 2 hours at room temperature, then was diluted with 10 mL of $H_2O$. The resulting solution was extracted with dichloromethane and the organic layer was concentrated in vacuo The residue obtained was purified using flash column chromatography on silica gel eluted with dichloromethane/methanol (100:1). The crude product was re-crystallized from a 10:1 mixture of pentane:tetrahydrofuran to provide 0.67 g (47%) of compound 16c as a solid.

LC-MS: (ES, m/z): 611 $[M+H]^+$H-NMR: (300 MHz, DMSO, ppm): δ 7.96 (dd, J=12.3, 7.1 Hz, 2H), 7.66 (ddt, J=24.8, 21.7, 8.2 Hz, 9H), 5.01 (s, 1H), 4.75 (d, J=14.8 Hz, 2H), 4.07 (s, 5H), 2.69 (s, 1H), 2.33 (s, 1H), 1.84-1.63 (m, 7H), 1.52 (s, 6H), 1.26 (s, 6H), 1.12 (s, 6H).

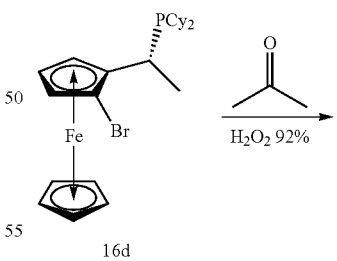

16d

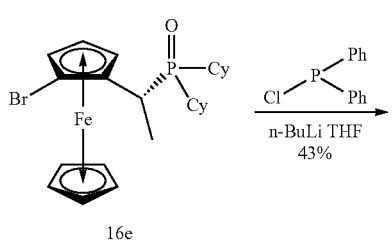

16e

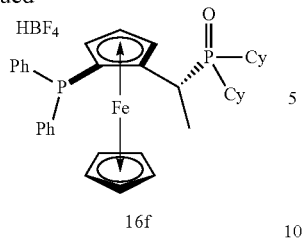

16f

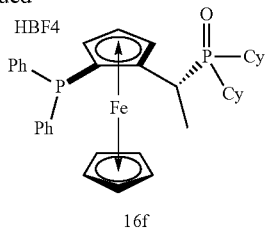

16f

Step C—Synthesis of Compound 16e

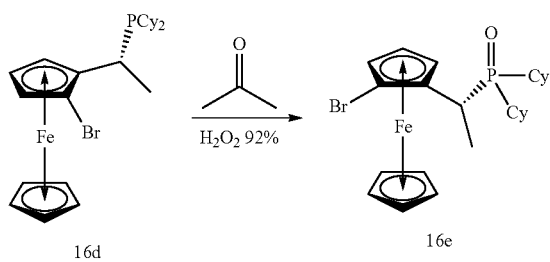

Into a 50-mL 3-necked round-bottom flask purged and maintained with an inert atmosphere of nitrogen, was placed compound 16d (2 g, 4.09 mmol, 1.00 equiv), propan-2-one (20 mL) and 30% hydrogen peroxide (930 mg, 8.17 mmol, 2.00 equiv). The reaction was allowed to stir for 4 hours at 40° C., then the reaction mixture was concentrated in vacuo to provide 2 g (92%) of compound 16e as a solid.

Step D—Synthesis of Compound 16f

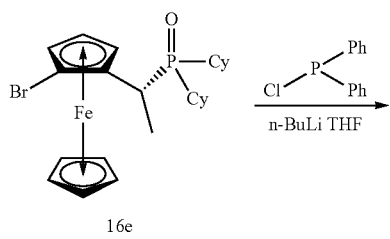

Into a 50-mL 3-necked round-bottom flask purged and maintained with an inert atmosphere of nitrogen, was placed compound 16e (1.5 g, 2.97 mmol, 1.00 equiv), tetrahydrofuran (15 mL). This was followed by the addition of butyllithium (228 mg, 3.56 mmol, 1.20 equiv) dropwise with stirring at −60° C. To this was added chlorodiphenylphosphane (786 mg, 3.56 mmol, 1.20 equiv) dropwise with stirring at −60° C. The solution was allowed to stir for 2 h at −60° C. To the mixture was added 40% HBF$_4$ solution (3.3 g, 15.2 mmol, 5.00 equiv) and the resulting reaction was allowed to stir for 2 hours at room temperature. The resulting solution was diluted with of H$_2$O and extracted with 20 mL of dichloromethane and the organic layer was collected and concentrated in vacuo. The residue obtained was purified using flash column chromatography on silica gel, eluting with dichloromethane/methanol (100:1). This resulted in 1.3 g crude HBF$_4$ salt. The crude salt was taken up in MTBE (10 mL) and stirred for 1 hour under nitrogen atmosphere, then the reaction was filtered and the collected solids were dried to provide 0.85 g (43%) of 16f as a solid. LC-MS: (ES, m/z): 611 [M+H]$^+$ H-NMR: (300 MHz, DMSO, ppm): δ 7.64 (ddt, J=7.8, 5.2, 2.8 Hz, 2H), 7.39 (td, J=3.1, 1.5 Hz, 3H), 7.27-7.15 (m, 5H), 4.63 (t, J=2.6 Hz, 1H), 4.51 (t, J=2.5 Hz, 1H), 4.38-4.30 (m, 1H), 3.28 (s, 3H), 1.79 (s, 1H), 1.61 (dt, J=16.1, 8.1 Hz, 5H), 1.44 (dd, J=22.4, 12.6 Hz, 9H), 1.28-0.91 (m, 11H), 0.75 (s, 3H).

Example 16

Preparation of Compound 26

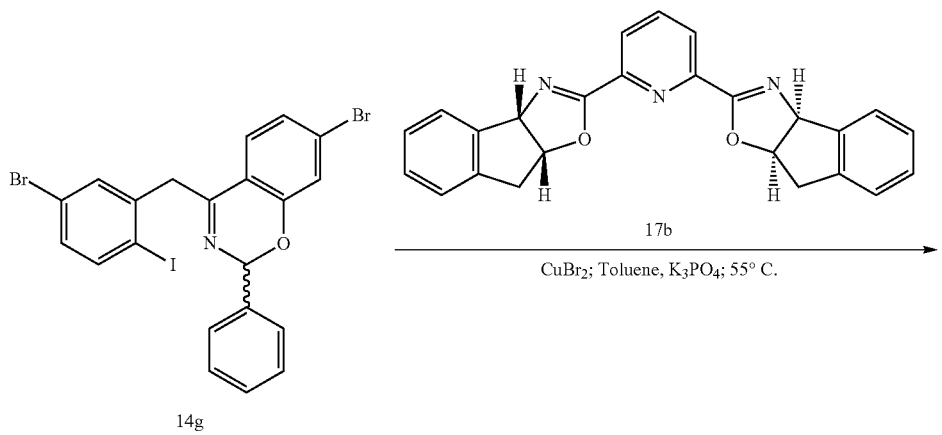

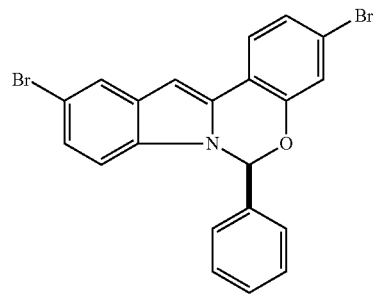

26

In a glove box, a slurry of copper(II) bromide (14.3 mg, 0.064 mmol) and compound 17b (commercially available, 25.2 mg, 0.064 mmol) in toluene (4 mL) was agitated about 16 h at room temperature. A portion of the resulting catalyst slurry (0.038 mL; about 4 mol % catalyst) was then added into a mixture of compound 14g (8.8 mg, 0.015 mmol) in toluene (0.225 mL) with stirring followed by $K_3PO_4$ (12.7 mg, 0.06 mmol). The resulting mixture was heated to about 55° C. and held at about 55° C. with stirring for about 27 h to provide compound 26 in 78% ee.

Example 17

Preparation of Compounds 15-25

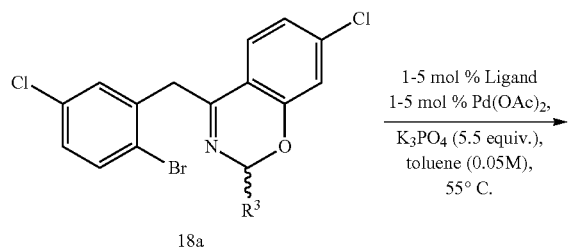

18a

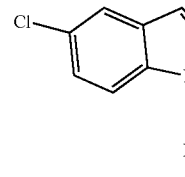

18b

Under a nitrogen atmosphere inside a glovebox, a 0.025 M solution of palladium acetate in anhydrous toluene was added to 1.0 mole equivalent of the ligand and the mixture was agitated at room temperature between 0.5 and 2 h (8 mL catalyst stock solution was prepared for 7e and 2 mL of stock solution was prepared for Ligand 18c, which is commercially available). A portion of the catalyst mixture (0.14 mL; 1 mol % catalyst) was then added to a mixture of compound 18a (0.35 mmol) in toluene (6.86 mL) followed by $K_3PO_4$ (409 mg, 1.93 mmol). The resulting mixture was heated to about 55° C. and held at about 55° C. with agitation at 1200 rpm for about 24 h to provide compound 18b. The absolute configurations of the compounds of 18b, where indicated, were confirmed was using X-ray analysis.
Wherein the structure of Ligand 7e and Ligand 18c are as follows:

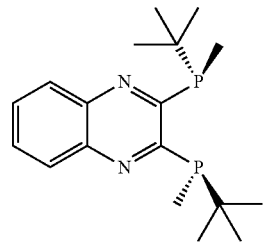 [SMILES: C[P@@](c1nc2ccccc2nc1[P@](C)C(C)(C)C)C(C)(C)C]

7e

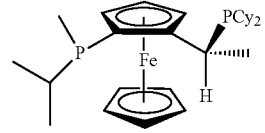

18c

| Compound | $R^3$ | Ligand | Yield (%) | % ee | % Pd* |
|---|---|---|---|---|---|
| 15 | 2-Me phenyl | 7e | 93 | 93 | 1 |
| 16 | 2-OMe phenyl | 7e | 94 | 94 | 1 |
| 17 | 2-$CO_2$Et Phenyl | 7e | 97 | 93 | 1 |
| 18 | 3-CN Phenyl | 7e | 95 | 96 | 2 |
| 19 | 4-pyridyl | 7e | 86 | 87 | 5 |
| 20 | 4-$CO_2$Et Phenyl | 7e | 95 | 95 | 2 |
| 21 | 4-OMe Phenyl | 7e | 94 | 95 | 1 |
| 22 | 4-$NO_2$ Phenyl | 7e | 90 | 88 | 2 |
| 23 | cyclohexyl | 18c | 94 | 89 | 5 |
| 24 | —$CH_2CH_2$Ph | 18c | 74 | 76 | 5 |
| 25 | isopropyl | 18c | 89 | 82 | 5 |

Compound 15: $[\alpha]_D^{25}=-325$ (c=1.11 in ethyl acetate). $^1$H NMR (500 MHz, CDCl$_3$): δ (ppm) 7.63 (d, 1H, J=11 Hz), 7.627 (s, 1H), 7.30-7.27 (m, 2H), 7.20 (s, 1H), 7.07 (dd, 1H, J=8.5, 2.0 Hz), 7.03-6.98 (m, 3H), 6.87 (s, 1H), 6.55 (d, 1H, J=8.5 Hz), 6.45 (d, 1H, J=8.0 Hz), 2.59 (s, 3H). $^{13}$C NMR (125 MHz, CDCl$_3$) δ (ppm) 150.1, 137.3, 134.5, 133.41, 133.39, 132.9, 131.3, 130.2, 130.1, 126.9, 126.5, 126.3, 124.8, 123.5, 122.9, 120.2, 118.1, 116.5, 110.8, 96.6, 83.7, 19.3. HRMS TOF MS (m/z): [M+H]$^+$ calcd for [$C_{22}H_{15}Cl_2$NO H] 380.0603; found 380.0612. FTIR(neat): 3068, 1606, 1571, 1550, 1428, 1440, 1218 cm$^{-1}$.

Compound 16: $[\alpha]_D^{25}=-170=0.98$ in ethyl acetate). $^1$H NMR (500 MHz, CDCl$_3$): δ (ppm) 7.64 (d, 1H, J=8.0 Hz), 7.60 (d, 1H, J=2.0 Hz), 7.54 (s, 1H), 7.33 (td, 1H, J=8.5, 1.5 Hz), 7.06 (dd, 1H, J=8.5, 2.0 Hz), 7.02-6.99 (m, 3H), 6.86

(s, 1H), 6.75-6.72 (m, 2H), 6.50 (dd, 1H, J=7.5, 1.5 Hz), 3.99 (s, 3H). $^{13}$C NMR (125 MHz, CDCl$_3$) δ (ppm) 157.3, 150.2, 134.5, 133.2, 132.8, 131.4, 130.2, 127.3, 126.4, 124.7, 124.0, 123.2, 122.7, 120.7, 120.1, 118.4, 116.4, 111.1, 110.8, 96.3, 79.9, 55.8. HRMS TOF MS (m/z): [M+H]$^+$ calcd for [C$_{22}$H$_{15}$Cl$_2$NO$_2$ H] 396.0553; found 396.0563. FTIR(neat): 3092, 1597, 1572, 1550, 1447, 1429, 1218 cm$^{-1}$.

Compound 17: [α]$_D^{25}$=−340 (c=1.07 in ethyl acetate). $^1$H NMR (500 MHz, CDCl$_3$): δ (ppm) 8.20 (s, 1H), 7.93 (dd, 1H, J=8.0, 1.5 Hz), 7.65 (d, 1H, J=2.0 Hz), 7.58 (d, 1H, J=8.5 Hz), 7.37 (td, 1H, J=8.0, 1.0 Hz), 7.20 (td, 1H, J=8.0, 1.0 Hz), 7.09 (dd, 1H, J=8.5, 2.0 Hz), 7.02 (dd, 1H, J=8.5, 2.0 Hz), 6.96 (d, 1H, J=9.0 Hz), 6.90 (d, 1H, J=2.0 Hz), 6.87 (s, 1H), 6.25 (d, 1H, J=8.0 Hz), 4.54 (q, 2H, J=7.5 Hz); 1.51 (t, 3H, J=7.5 Hz). $^{13}$C NMR (125 MHz, CDCl$_3$) δ (ppm) 167.4, 149.5, 136.3, 134.6, 133.5, 132.3, 131.9, 130.8, 130.6, 129.9, 129.6, 126.7, 126.6, 124.7, 123.5, 123.1, 120.3, 118.4, 116.4, 110.6, 96.6, 80.9, 61.7, 14.3. HRMS TOF MS (m/z): [M+H]$^+$ calcd for [C$_{24}$H$_{17}$Cl$_2$NO$_3$ H] 438.0658; found 438.0678. FTIR(neat): 2978, 1721, 1610, 1573, 1429, 1360, 1256 cm$^{-1}$.

Compound 18: [α]$_D^{25}$=−415 (c=0.975 in ethyl acetate). $^1$H NMR (500 MHz, CDCl$_3$): δ (ppm) 7.67 (d, 1H, J=1.5 Hz), 7.62-7.59 (m, 2H), 7.41 (t, 1H, J=8.0 Hz), 7.26 (d, 1H, J=2.5 Hz), 7.21-7.20 (m, 2H), 7.14 (dd, 1H, J=8.5 Hz, 2.0 Hz), 7.08-7.04 (m, 2H), 6.92 (d, 1H, J=9.0 Hz), 6.88 (s, 1H). $^{13}$C NMR (125 MHz, CDCl$_3$) δ (ppm) 148.9, 138.2, 134.9, 133.32, 133.30, 131.3, 130.9, 130.1, 130.0, 129.9, 127.1, 125.0, 124.0, 123.5, 120.7, 118.5, 117.9, 116.3, 113.3, 109.9, 97.5, 82.7. HRMS TOF MS (m/z): [M+H]$^+$ calcd for [C$_{22}$H$_{12}$Cl$_2$N$_2$O H] 391.0405; found 391.0401. FTIR(neat): 3073, 2230, 1607, 1566, 1551, 1428 cm$^{-1}$.

Compound 19: [α]$_D^{25}$=−407 (c=0.95 in ethyl acetate). $^1$H NMR (500 MHz, CDCl$_3$): δ (ppm) 7.96 (d, 2H, J=8.5 Hz), 7.65 (d, 1H, J=2.0 Hz), 7.58 (d, 1H, J=8.0 Hz), 7.20 (s, 1H), 7.11-7.09 (m, 3H), 7.06-7.03 (m, 2H), 6.87 (d, 1H, J=8.5 Hz), 6.86 (s, 1H), 4.34 (q, 2H, J=7.0 Hz), 1.35 (t, 3H, J=7.0 Hz). $^{13}$C NMR (125 MHz, CDCl$_3$) δ (ppm) 165.7, 149.5, 140.8, 134.7, 133.5, 131.9, 131.8, 130.1, 130.0, 126.8, 126.7, 124.9, 123.7, 123.2, 120.5, 118.5, 116.5, 110.3, 97.1, 83.7, 61.2, 14.2. HRMS TOF MS (m/z): [M+H]$^+$ calcd for [C$_{24}$H$_{17}$Cl$_2$NO$_3$ H] 438.0658; found 438.0668. FTIR(neat): 2940, 1714, 1607, 1569, 1439, 1429, 1364, 1274 cm$^{-1}$.

Compound 20: [α]$_D^{25}$=−367 (c=0.965 in ethyl acetate). $^1$H NMR (500 MHz, CDCl$_3$): δ (ppm) 7.62 (d, 1H, J=1.5 Hz), 7.60 (d, 1H, J=8.5 Hz), 7.06-7.02 (m, 6H), 6.85-6.83 (m, 3H), 6.69 (d, 1H, J=8.5 Hz), 3.78 (s, 3H). $^{13}$C NMR δ (ppm) (125 MHz, CDCl$_3$) δ (ppm) 160.7, 150.2, 134.5, 133.6, 132.5, 130.1, 128.4, 128.2, 126.5, 124.8, 123.4, 122.8, 120.2, 118.4, 116.6, 114.2, 110.9, 96.7, 84.6, 55.3. HRMS TOF MS (m/z): [M+H]$^+$ calcd for [C$_{22}$H$_{15}$Cl$_2$NO$_2$ H] 396.0553; found 396.0555. FTIR(neat): 2933, 1607, 1569, 1510, 1445, 1431 cm$^{-1}$.

Compound 21: [α]$_D^{25}$=−398 (c=1.01 in ethyl acetate). $^1$H NMR (500 MHz, CDCl$_3$): δ (ppm) 8.12 (d, 2H, 9.0 Hz), 7.68 (d, 1H, J=2.0 Hz), 7.59 (d, 1H, J=8.0 Hz), 7.29 (s, 1H), 7.17-7.14 (m, 3H), 7.08-7.05 (m, 2H), 6.98 (d, 1H, J=8.5 Hz), 6.89 (s, 1H). $^{13}$C NMR (125 MHz, CDCl$_3$): δ (ppm) 149.0, 148.7, 143.1, 135.0, 133.4, 131.4, 130.0, 127.7, 127.1, 125.0, 124.2, 124.1, 123.5, 120.7, 118.5, 116.4, 110.0, 97.5, 82.7. HRMS TOF MS (m/z): [M+H]$^+$ calcd for [C$_{21}$H$_{12}$Cl$_2$N$_2$O$_3$ H] 411.0298; found 411.0312. FTIR(neat): 3072, 1608, 1571, 1523, 1429, 1342 cm$^{-1}$.

Compound 22: [α]$_D^{25}$=−413 (c=0.558 in ethyl acetate). $^1$H NMR (500 MHz, CDCl$_3$): δ (ppm) 8.53 (d, 2H, J=6.0 Hz), 7.68 (d, 1H, J=2.0 Hz), 7.58-7.56 (m, 1H), 7.20 (s, 1H), 7.17 (dd, 1H, J=8.5, 2.0 Hz), 7.07-7.03 (m, 3H), 6.88-6.87 (m, 3H). $^{13}$C NMR (125 MHz, CDCl$_3$): δ (ppm) 150.6, 149.0, 145.1, 134.9, 133.5, 131.3, 130.0, 127.0, 125.0, 124.0, 123.5, 121.0, 120.7, 118.5, 116.4, 109.9, 97.4, 82.3. HRMS TOF MS (m/z): [M+H]$^+$ calcd for [C$_{20}$H$_{12}$Cl$_2$N$_2$O H] 367.0399; found 367.0401. FTIR(neat): 3057, 1608, 1592, 1572, 1448, 1430, 1409 cm$^{-1}$.

Compound 23: [α]$_D^{25}$=−222 (c=0.99 in ethyl acetate). $^1$H NMR (500 MHz, CDCl$_3$): δ (ppm) 7.59-7.57 (m, 2H), 7.20-7.15 (m, 2H), 7.10-7.07 (m, 2H), 6.71 (s, 1H), 5.94 (d, 1H, J=8.5 Hz), 1.96-1.90 (m, 2H), 1.75-1.73 (m, 1H), 1.64-1.60 (m, 2H), 1.21-0.98 (m, 6H). $^{13}$C NMR (125 MHz, CDCl$_3$): δ (ppm) 149.9, 134.6, 133.8, 130.8, 129.6, 125.9, 124.8, 123.1, 122.5, 120.2, 118.1, 117.0, 110.4, 96.4, 87.7, 43.0, 29.0, 28.5, 25.8, 25.5, 25.3. FIRMS TOF MS (m/z): [M+H]$^+$ calcd for [C$_{21}$H$_{19}$Cl$_2$NO H] 372.0916; found 372.0928. FTIR(neat): 2928, 2845, 1607, 1572, 1548, 1444, 1430 cm$^{-1}$.

Compound 24: [α]$_D^{25}$=−148 (c=0.86 in ethyl acetate). $^1$H NMR (500 MHz, CDCl$_3$): δ (ppm) 7.59-7.58 (m, 2H), 7.34-7.31 (m, 2H), 7.27-7.25 (m, 1H), 7.20-7.18 (m, 2H), 7.13 (dd, 1H, J=8.5, 2.0 Hz), 7.10 (dd, 1H, J=8.0, 2.0 Hz), 7.06 (d, 1H, J=2.0 Hz), 6.95 (d, 1H, J=8.5 Hz), 6.72 (s, 1H), 6.22 (dd, 1H, J=9.0, 4.0 Hz), 2.86-2.74 (m, 2H), 2.31-2.26 (m, 1H), 2.04-1.99 (m, 1H). $^{13}$C NMR (125 MHz, CDCl$_3$): δ (ppm) 149.0, 139.8, 134.7, 132.5, 130.7, 130.0, 128.6, 128.4, 126.5, 126.3, 124.9, 123.4, 122.7, 120.3, 118.5, 116.4, 109.6, 96.4, 83.2, 35.2, 30.8. HRMS TOF MS (m/z): [M+H]$^+$ calcd for [C$_{23}$H$_{17}$Cl$_2$NO H] 394.0760; found 394.0774. FTIR(neat): 3077, 3023, 2913, 1609, 1570, 1551, 1443, 1428 cm$^{-1}$.

Compound 25: [α]$_D^{25}$=−281 (c=0.50 in ethyl acetate). $^1$H NMR (500 MHz, CDCl$_3$): δ (ppm) 7.59-7.56 (m, 2H), 7.21-7.15 (m, 2H), 7.09-7.06 (m, 2H), 6.72 (s, 1H), 5.92 (d, 1H, J=8.5 Hz), 2.31-2.24 (m, 1H), 1.06 (d, 3H, J=5.0 Hz), 0.82 (d, 3H, J=5.0 Hz). $^{13}$C NMR (125 MHz, CDCl$_3$): δ (ppm) 149.9, 134.6, 133.7, 130.8, 129.7, 126.0, 124.7, 123.1, 122.6, 120.2, 118.0, 117.0, 110.4, 96.4, 88.5, 34.0, 18.6, 18.1. HRMS TOF MS (m/z): [M+H]$^+$ calcd for [C$_{18}$H$_{15}$Cl$_2$NO H] 332.0603; found 332.0606. FTIR(neat): 2963, 2919, 1607, 1572, 1549, 1443, 1431 cm$^{-1}$.

Example 18

Preparation of Compounds 29a and 29b

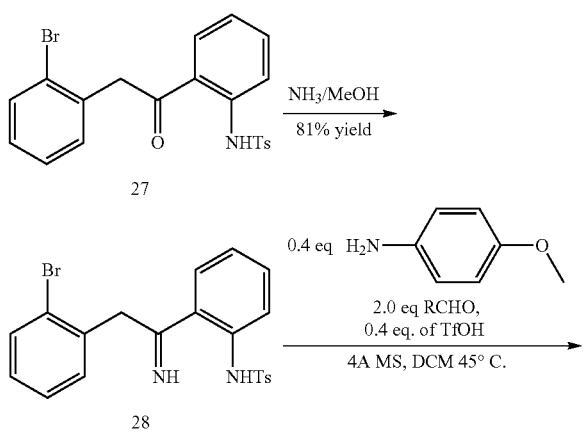

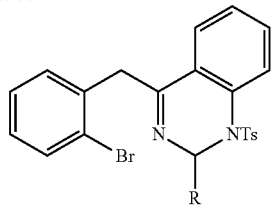
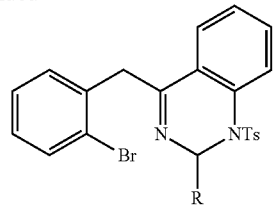

29a: R = Ph
29b: R = —CH₂CH₂Ph

Step A—Synthesis of compound 28

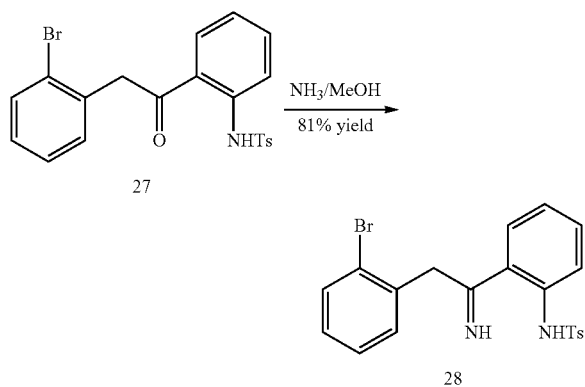

The solution of N-(2-(2-(2-bromophenyl)acetyl)phenyl)-4-methylbenzenesulfonamide (27) (1.9 g, 4.28 mmol) in ammonia (19.55 mL, 137 mmol) (7N in MeOH) was allowed to stir at room temperature for about 15 hours. There are lots of precipitates generated (yellow). The solid was collected by vacuum filtration and washed with MeOH, then the solid was dried under with N2 flow at room temperature. to provide N-(2-(2-(2-bromophenyl)-1-iminoethyl)phenyl)-4-methylbenzenesulfonamide (28) (1.54 g, 81% yield). The product was used for next step without any further purification. NMR (500 MHz, CDCl₃): δ (ppm) 14.0 (br, 1H), 9.46 (br, 1H), 7.74-7.67 (m, 5H), 7.36 (qd, 2H, J=7.5, 1.0 Hz), 7.27 (td, 1H, J=8.0, 2.0 Hz), 7.20 (d, 2H, J=8.5 Hz), 7.15 (dd, 1H, J=7.5, 1.5 Hz), 7.05 (td, 1H, J=8.0, 1.0 Hz), 4.17 (s, 2H), 2.37 (s, 3H). ¹³C NMR (125 MHz, CDCl₃): δ (ppm) 175.6, 143.2, 140.3, 137.3, 133.6, 133.5, 132.5, 132.0, 129.9, 129.4, 128.9, 128.2, 127.2, 125.8, 122.1, 121.7, 119.2, 44.6, 21.5. HRMS TOF MS (m/z): [M+H]⁺ calcd for [C₂₁H₁₉BrN₂O₂S H] 443.0423; found 443.0426. FTIR(neat): 3059 (br), 1601, 1535, 1481, 1438, 1278, 1253 cm⁻¹.

Step A—Synthesis of Compounds 29a and 29b

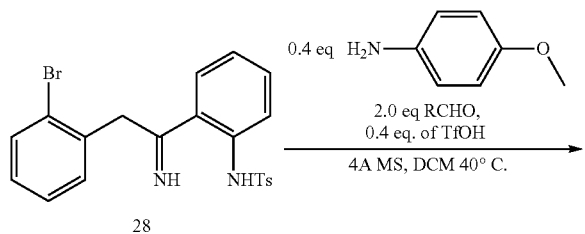

A suspension of 4 Å molecular sieves (3 g), 4-methoxyaniline (0.167 g, 1.353 mmol), RCHO (6.77 mmol), compound 28 (1.50 g, 3.38 mmol) in DCM (15.00 mL) was charged trifluoromethanesulfonic acid (0.118 mL, 1.353 mmol). Then the mixture was heated to 40° C. and allowed to stir at this temperature for 48 hours. The mixture was then filtered through filter aid and the filtrate was concentrated in vacuo and purified using flash chromatography (elutent: Hexanes/ethyl acetate: from 92/8 to 95/5).

4-(2-bromobenzyl)-2-phenyl-1-tosyl-1,2-dihydroquinazoline (29a): solid in 78% yield. ¹H NMR (500 MHz, CDCl₃): δ (ppm) 7.83 (dd, 1H, J=8.0, 1.0 Hz), 7.57-7.55 (m, 1H), 7.47-7.39 (m, 5H), 7.33 (dd, 1H, J=8.0, 1.5 Hz), 7.27-7.15 (m, 7H), 7.11-7.06 (m, 2H), 6.55-6.53 (m, 1H), 4.11 (d, J=15.0 Hz), 3.68 (d, 1H, J=15.0 Hz), 2.45 (s, 3H). ¹³C NMR (125 MHz, CDCl₃): δ (ppm) 162.9, 143.8, 137.5, 136.4, 136.1, 134.7, 132.7, 132.3, 130.7, 129.5, 128.3, 128.0, 127.9, 127.5, 127.18, 127.17, 127.0, 126.4, 125.0, 124.8, 124.4, 72.5, 41.1, 21.6. HRMS TOF MS (m/z): [M+H]⁺ calcd for [C₂₈H₂₃BrN₂O₂S H] 531.0736; found 531.0756. FTIR(neat): 3055, 1635, 1598, 1449, 1346, 1167 cm⁻¹.

4-(2-bromobenzyl)-2-phenethyl-1-tosyl-1,2-dihydroquinazoline (29b): yellowish syrup in 64% yield. ¹H NMR (500 MHz, CD₃CN): δ (ppm) 7.74 (dd, 1H, J=8.0, 1.0 Hz), 7.60-7.56 (m, 1H), 7.54-7.51 (m, 2H), 7.36 (td, 1H, J=7.5, 1.0 Hz), 7.26-7.18 (m, 7H), 7.16-7.09 (m, 4H), 6.66 (dd, 1H, J=7.5, 2.0 Hz), 5.84 (dd, 1H, J=8.5, 5.0 Hz), 4.01 (d, 1H, J=15.0 Hz), 3.33 (d, 1H, J=15.0 Hz), 2.73-2.64 (m, 2H), 2.41 (s, 3H), 1.84-1.77 (m, 1H), 1.54-1.46 (m, 1H). ¹³C NMR (125 MHz, CD₃CN): δ (ppm) 161.7, 145.5, 142.6, 138.0, 136.8, 135.2, 133.4, 133.2, 132.7, 130.7, 129.5, 129.42, 129.39, 128.5, 128.4, 128.3, 128.0, 126.9, 126.1, 125.9, 125.2, 72.5, 41.5, 34.8, 32.1, 21.7. HRMS TOF MS (m/z): [M+H]⁺ calcd for [C₃₀H₂₇BrN₂O₂S H] 559.1049; found 559.1063. FTIR(neat): 3023, 1629, 1596, 1451, 1347 cm⁻¹.

Example 19

Preparation of Compounds 30a and 30b

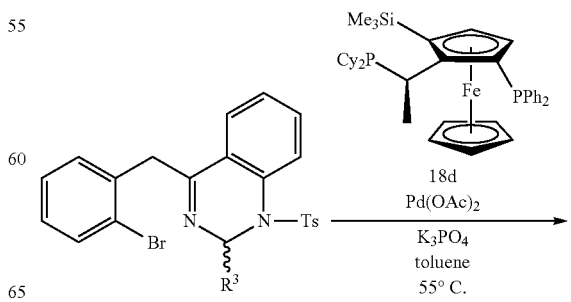

-continued

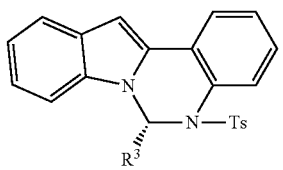
30

Under a nitrogen atmosphere inside a glovebox, a 0.025 M solution of palladium acetate in anhydrous toluene was added to 5.0 mole equivalent of the ligand and the mixture was agitated at room temperature between 0.5 and 2 h (2 mL of stock solution was prepared for 18d). A portion of the catalyst mixture (0.14 mL; 1 mol % catalyst) was then added to a mixture of compound 29 (0.35 mmol) in toluene (6.86 mL) followed by $K_3PO_4$ (409 mg, 1.93 mmol). The resulting mixture was heated to about 55° C. and held at about 55° C. with agitation at 1200 rpm for about 24 h to provide a compound of formula 30. The absolute configurations of the compounds of 30, where indicated, were confirmed was using X-ray analysis.

| Compound | $R^3$ | Yield (%) | % ee |
|---|---|---|---|
| 30a | Phenyl | 85 | 94 |
| 30b | —$CH_2CH_2$-Phenyl | 95 | 90 |

Compound 30a: $[\alpha]_D^{25}=-187$ (c=1.225 in ethyl acetate). $^1$H NMR (500 MHz, CDCl$_3$): δ (ppm) 7.73-7.70 (m, 1H), 7.64 (s, 1H), 7.53 (d, 1H, J=8.0 Hz), 7.51-7.48 (m, 1H), 7.32-7.23 (m, 5H), 7.17-7.12 (m, 4H), 6.98-6.96 (m, 2H), 6.92-6.89 (m, 2H), 6.54 (d, 1H, J=8.0 Hz), 6.42 (s, 1H), 2.09 (s, 3H). $^{13}$C NMR (125 MHz, CDCl$_3$): δ (ppm) 143.6, 136.6, 135.9, 132.8, 130.9, 130.4, 129.3, 128.6, 128.5, 128.4, 128.2, 128.1, 128.0, 126.5, 126.2, 125.9, 123.8, 122.8, 120.7, 120.6, 108.8, 97.4, 68.0, 21.2. HRMS TOF MS (m/z): [M+H]$^+$ calcd for [$C_{28}H_{22}N_2O_2S$ H] 451.1475; found 451.1489. FTIR(neat): 3025, 1488, 1465, 1448, 1352, 1338 cm$^{-1}$. The absolute configuration was assigned as R based on X-ray analysis (crystallized from ethyl acetate/hexanes).

Compound 30b: $[\alpha]_D^{25}=-328$ (c=0.75 in ethyl acetate). $^1$H NMR (500 MHz, CDCl$_3$): δ (ppm) 7.81 (dd, 1H, J=7.0, 1.5 Hz, 1H), 7.54 (dd, 1H, J=7.5, 2.0 Hz), 7.45 (d, 1H, J=8.0 Hz), 7.43-7.36 (m, 2H), 7.31-7.30 (m, 2H), 7.24-7.19 (m, 4H), 7.12-7.07 (m, 2H), 6.81 (d, 2H, J=8.5 Hz), 6.51-6.47 (m, 3H), 6.31 (s, 1H), 2.93-2.88 (m, 1H), 2.83-2.77 (m, 1H), 2.07-2.01 (m, 1H), 2.02 (s, 3H), 1.97-1.91 (m, 1H). $^{13}$C NMR (125 MHz, CDCl$_3$): δ (ppm) 143.5, 140.3, 134.8, 132.7, 130.1, 129.5, 128.52, 128.51, 128.46, 128.3, 128.12, 128.10, 126.4, 126.2, 125.7, 123.9, 122.5, 120.6, 120.2, 108.4, 97.1, 66.4, 36.2, 31.3, 21.2. HRMS TOF MS (m/z): [M+H]$^+$ calcd for [$C_{30}H_{26}N_2O_2S$ H] 479.1788; found 479.1811. FTIR(neat): 2921, 1722, 1595, 1574, 1552, 1447, 1406, 1447, 1354 cm$^{-1}$.

Example 20

Alternate Preparation of Compound 9

In a glovebox under nitrogen atmosphere, a 0.1 M solution of KOtBu in toluene (700 μl, 70 μmol, 1.0 eq.) was slowly added to a mixture of Ligand 19a (commercially available, 49 mg, 70 μmol, 1.0 eq.) in 700 μl toluene at about 25° C. To a portion of the resulting mixture (350 μl) was added a solution of tris(dibenzylideneacetone)dipalladium (0) (8.0 mg, 8.8 μmol, 1.0 eq. Pd relative to ligand) in 350 μL anhydrous toluene. The mixture was agitated for about 0.5 h at about 25° C. The catalyst mixture (700 about 5 mol % loading Pd) was then added to a solution of 7d (157 mg, 0.35 mmol, 1.0 eq.) in 6.30 mL toluene with agitation at room temperature followed by $K_3PO_4$ (409 mg, 1.93 mmol, 5.5 eq.) with agitation prior to heating to 55° C. The resulting mixture agitated at about 55° C. for about 20 h to provide compound 9 in 87% ee.

Example 21

Alternate Preparation of Compound 9

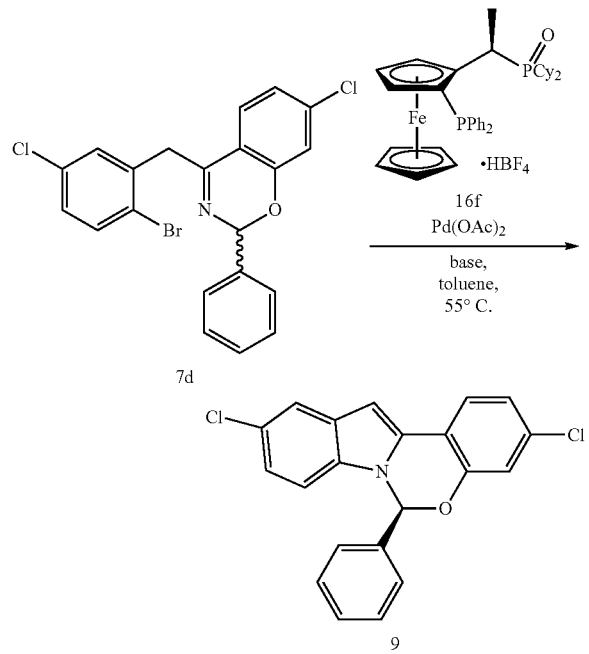

In a glovebox under nitrogen atmosphere, a 0.1 M solution of KOtBu in toluene (700 μl, 70 μmol, 1.0 eq.) was slowly added to a mixture of Ligand 16f (49 mg, 70 μmol, 1.0 eq.) in 700 μl toluene at about 25° C. To portion of the resulting mixture (700 μl) was added a solution of palladium acetate (3.9 mg, 18 μmol, 0.5 eq. Pd relative to ligand) in 350 μL anhydrous toluene. The mixture was agitated for about 0.5 h at about 25° C. The catalyst mixture (1.05 mL, about 5 mol % loading Pd) was then added to a solution of 7d (157 mg, 0.35 mmol, 1.0 eq.) in 6.30 mL toluene with agitation at room temperature followed by K₃PO₄ (409 mg, 1.93 mmol, 5.5 eq.) with agitation prior to heating to 55° C. The resulting mixture agitated at about 55° C. for about 20 h to provide compound 9 in about 87% ee.

Example 22

Alternate Preparation of Compound 9

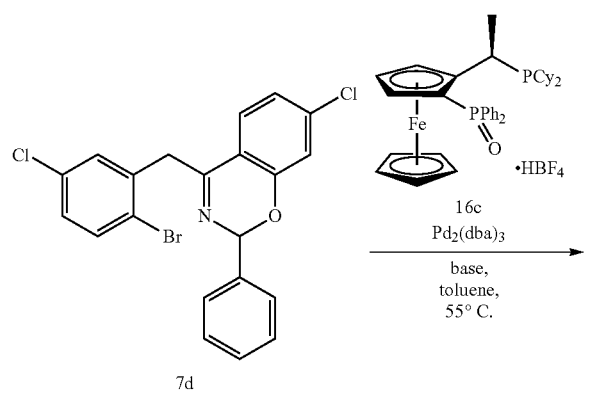

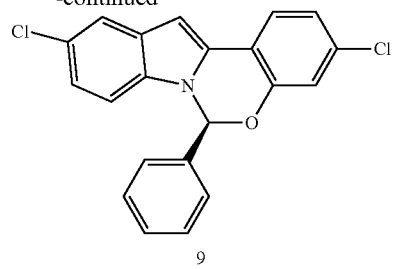

In a glovebox under nitrogen atmosphere, a 0.1 M solution of KOtBu in toluene (700 μl, 70 μmol, 1.0 eq.) was slowly added to a mixture of Ligand 16c (49 mg, 70 μmol, 1.0 eq.) in 700 μl tetrahydrofuran at about 25° C. To a portion of the resulting mixture (350 μl) was added a solution of tris(dibenzylideneacetone)dipalladium(0) (8.0 mg, 8.8 μmol, 1.0 eq. Pd relative to ligand) in 350 μL anhydrous toluene. The mixture was agitated for about 0.5 h at about 25° C. The catalyst mixture (700 about 5 mol % loading Pd) was then added to a solution of 7d (157 mg, 0.35 mmol, 1.0 eq.) in 6.30 mL toluene with agitation at room temperature followed by K₃PO₄ (409 mg, 1.93 mmol, 5.5 eq.) with agitation prior to heating to 55° C. The resulting mixture was agitated at 55° C. for about 20 hours to provide compound 9 in about 4% ee.

Example 23

Alternate Preparation of Compound 9 Using Inorganic Bases

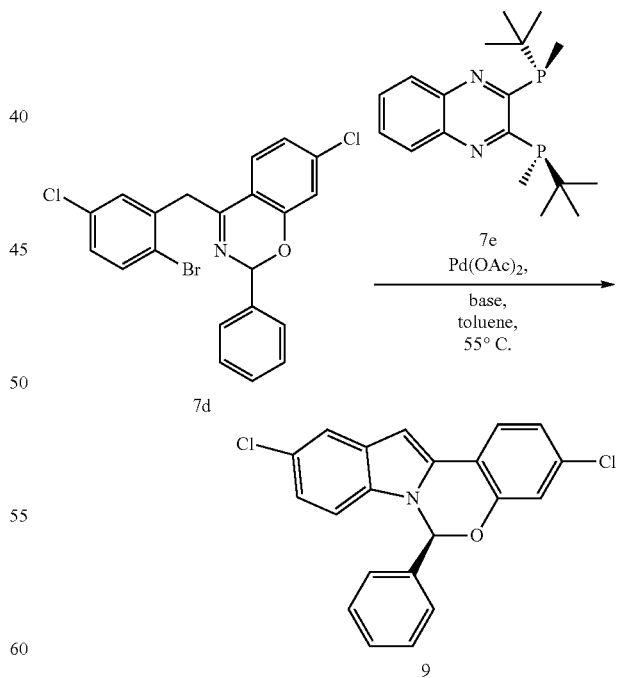

In a glovebox under nitrogen atmosphere, a solution of palladium acetate (14.4 mg, 64 μmol) in 8 mL anhydrous toluene was prepared. A 50 μL portion of this solution (0.09 mg, 4.0 μmol, about 0.10 eq. palladium acetate) was then added to 7e (0.42 µmol, 0.11 eq.). The resulting mixture was agitated for about 2 hours at about 35° C. A solution of 7d (1.8 mg, 4.0 µmol, 1.0 eq.) in 60 µL toluene was then added to a 50 µL portion of the catalyst mixture (about 10 mol % loading Pd) at room temperature followed by the base (30 µmol, 7.5 eq.) prior to heating to 55° C. The resulting mixture was agitated at about 55° C. for about 18 hours to provide compound 9 in 93-96% ee for the following bases: $K_3PO_4$, $K_2CO_3$, $KHCO_3$, KOAc, KF, LiOH, $Li_2CO_3$, $Na_2CO_3$, $Rb_2CO_3$, and $Cs_2CO_3$.

Example 24

Alternate Preparation of Compound 9 Using Organic Bases

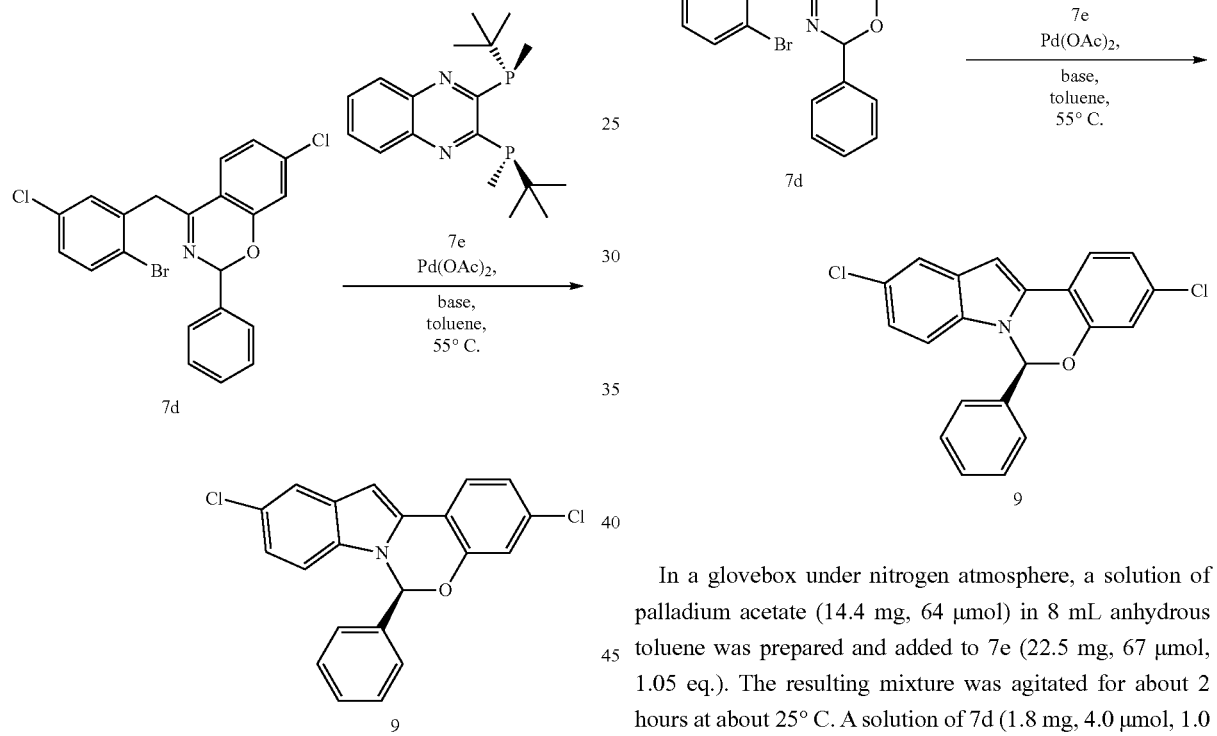

In a glovebox under nitrogen atmosphere, a solution of palladium acetate (14.4 mg, 64 µmol) in 8 mL anhydrous toluene was prepared. A 50 µL portion of this solution (0.09 mg, 4.0 µmol, about 0.10 eq. palladium acetate) was then added to 7e (0.42 µmol, 0.11 eq.). The resulting mixture was agitated for about 2 hours at about 35° C.

Substrate-Base Mixture Prep: A 0.15 M solution of base in toluene (1.0 mL, 4.4 µmol, 1.1 eq.) was added to a solution of compound 7d (59.2 mg, 132 µmole, 1.0 eq.) in 1 mL toluene portionwise at about −5° C. over about 10 minutes. and the mixture agitated about 0.5 hour. Reaction: 60 µl of the resulting substrate-base mixture (4 µmol substrate) was added to a 50 µL portion of catalyst mixture solution at room temp. with agitation prior to heating to 55° C. The resulting mixture was agitated at 55° C. for about 18 hours to provide compound 9 in 90-96% ee for the following bases: KOtBu, NaOtBu, KHMDS, NaHMDS, and LiHMDS.

Example 25

Alternate Preparation of Compound 9 Using Amine Bases

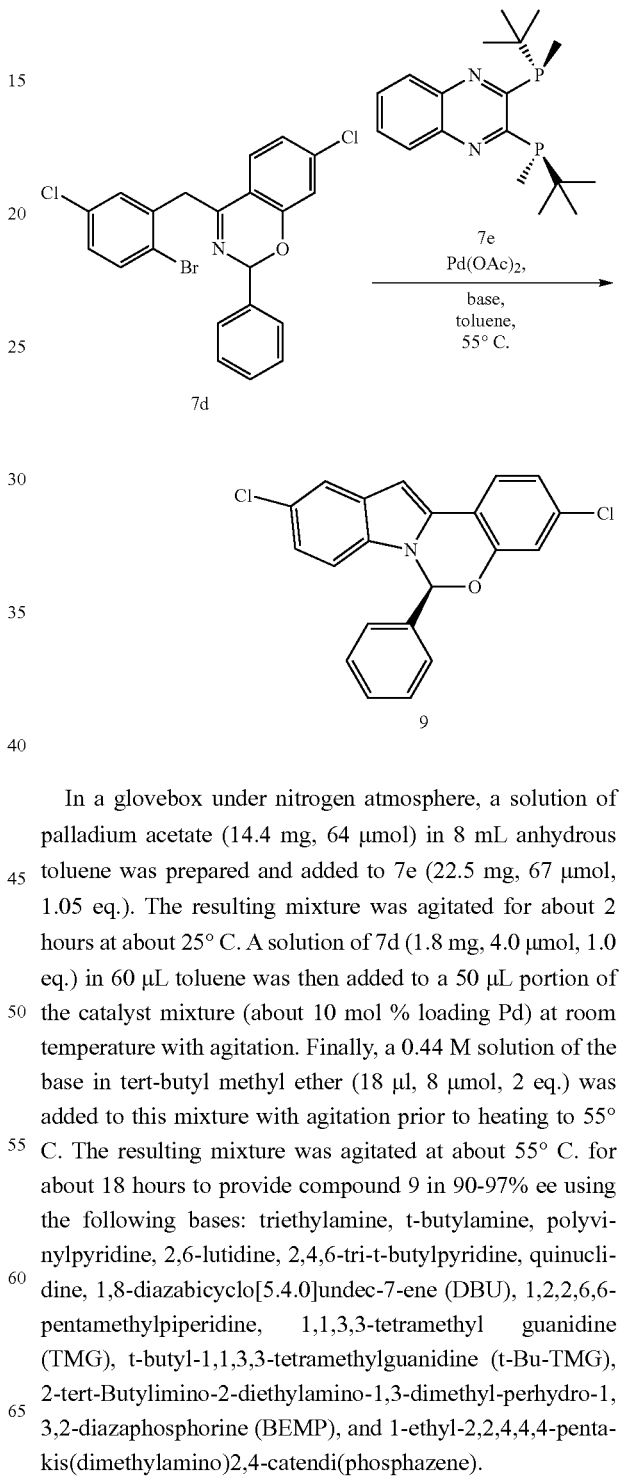

In a glovebox under nitrogen atmosphere, a solution of palladium acetate (14.4 mg, 64 µmol) in 8 mL anhydrous toluene was prepared and added to 7e (22.5 mg, 67 µmol, 1.05 eq.). The resulting mixture was agitated for about 2 hours at about 25° C. A solution of 7d (1.8 mg, 4.0 µmol, 1.0 eq.) in 60 µL toluene was then added to a 50 µL portion of the catalyst mixture (about 10 mol % loading Pd) at room temperature with agitation. Finally, a 0.44 M solution of the base in tert-butyl methyl ether (18 µl, 8 µmol, 2 eq.) was added to this mixture with agitation prior to heating to 55° C. The resulting mixture was agitated at about 55° C. for about 18 hours to provide compound 9 in 90-97% ee using the following bases: triethylamine, t-butylamine, polyvinylpyridine, 2,6-lutidine, 2,4,6-tri-t-butylpyridine, quinuclidine, 1,8-diazabicyclo[5.4.0]undec-7-ene (DBU), 1,2,2,6,6-pentamethylpiperidine, 1,1,3,3-tetramethyl guanidine (TMG), t-butyl-1,1,3,3-tetramethylguanidine (t-Bu-TMG), 2-tert-Butylimino-2-diethylamino-1,3-dimethyl-perhydro-1,3,2-diazaphosphorine (BEMP), and 1-ethyl-2,2,4,4,4-pentakis(dimethylamino)2,4-catendi(phosphazene).

Example 26

Alternate Preparation of Compound 9

In a glovebox under nitrogen atmosphere, a solution of palladium acetate (44.9 mg, 0.20 mmol) in 8 mL anhydrous toluene was prepared and was then added to 7e (66.9 mg, 0.20 mmol, 1.0 eq.). The resulting mixture was agitated for about 1.5 hours at about 25° C. A portion of the resulting catalyst mixture (700 µl, about 5 mol % loading Pd) was then added to a solution of 7d (157 mg, 0.35 mmol, 1.0 eq.) in 6.3 mL toluene with agitation at room temperature. Finally, 2-tert-butyl-1,1,3,3-tetramethylguanidine (73 µl, 61 mg, 357 µmol, 1.02 eq.) was added to this mixture with agitation prior to heating to 55° C. The resulting mixture was agitated at about 55° C. for about 24 hours to provide compound 9 in about 94% ee.

Example 27

Alternate Preparation of Compound 9

In a glovebox under nitrogen atmosphere, a solution of palladium acetate (44.9 mg, 0.20 mmol) in 8 mL anhydrous toluene was prepared and was then added to 7e (66.9 mg, 0.20 mmol, 1.0 eq.). The resulting mixture was agitated for about 1.5 hours at about 25° C. A portion of the resulting catalyst mixture (1.47 mL, about 3.5 mol % loading Pd) was then added to a solution of compound 7d (470 mg, 1.05 mmol, 1.0 eq.) in 3.79 mL toluene with agitation at room temperature. Finally, 2-tert-butylimino-2-diethylamino-1,3-dimethylperhydro-1,3,2-diazaphosphirine, polymer-bound (580 mg, 2.0-2.5 mmole/g loading, 1.2-1.5 mmol, 1.1-1.4 eq.) was added to this mixture with agitation prior to heating to 55° C. The resulting mixture was agitated at about 55° C. for about 21 hour, cooled to room temperature, the reaction filtered, the filtered solids washed with toluene (16 mL), and the combined filtrates concentrated in vacuo to provide 340 mg of compound 9 in about 94% ee.

Example 28

Alternate Preparation of Compound 9

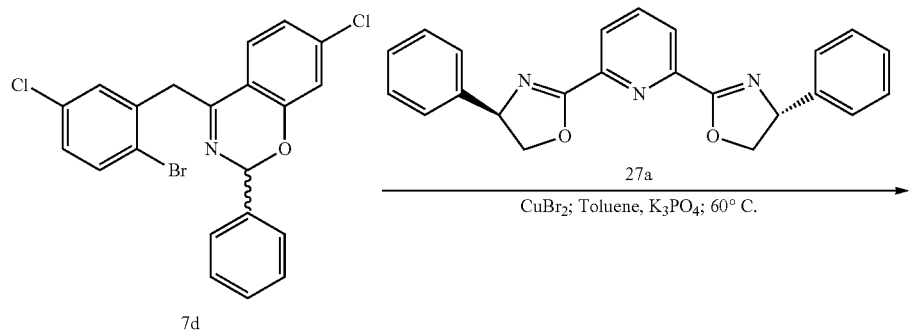

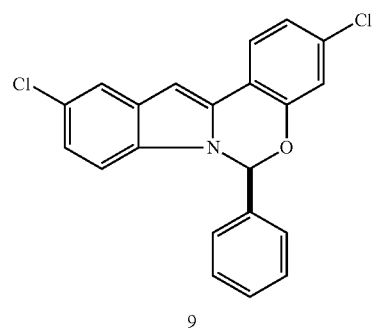

In a glove box, a slurry of copper(II) bromide (14.3 mg, 0.064 mmol) and compound 27a (commercially available, 24.8 mg, 0.067 mmol) in toluene (8 mL) was agitated about 19 hours at 50° C. A portion of the resulting catalyst slurry (0.019 mL; about 3.8 mol % catalyst) was then added into a mixture of compound 7d (1.8 mg, 0.004 mmol) in toluene (0.1 mL) with stirring followed by $K_3PO_4$ (6.4 mg, 0.03 mmol). The resulting mixture was heated to about 60° C. and held at about 60° C. with stirring for about 19 hours to provide compound 9 in 55% ee.

Example 29

Alternate Preparation of Compound 9

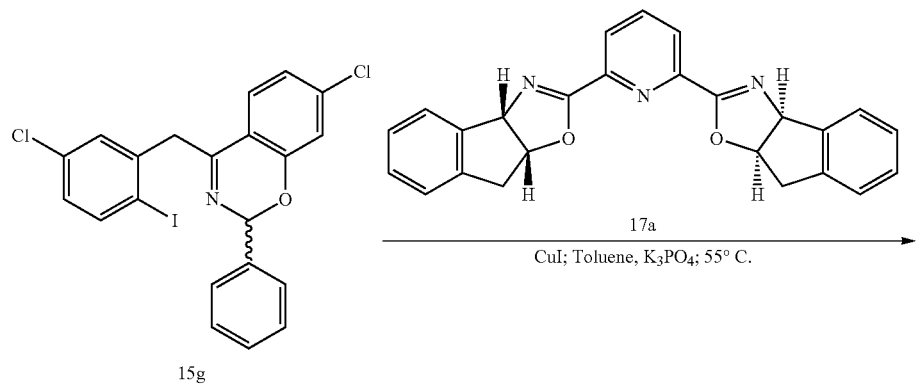

-continued

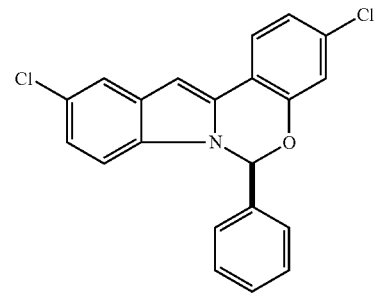

9

In a glove box, a slurry of copper(I) iodide (2.285 mg, 0.012 mmol, 6% cat.) and compound 17a (commercially available, 2.361 mg, 0.006 mmol, 3%) in toluene (3 mL) was heated to about 55° C. for about 2 h. The resulting catalyst slurry was then added into a mixture of compound 15g (99 mg, 0.2 mmol) and K$_3$PO$_4$ (170 mg, 0.8 mmol) in toluene (2 mL) with stirring. The resulting mixture was heated to about 55° C. and held at about 55° C. with stirring for about 19 hours to provide compound 9 in 76% ee.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A compound having the structure:

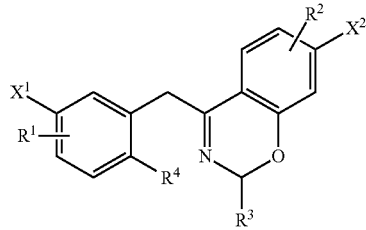

or a pharmaceutically acceptable salt thereof,
wherein:
X$^1$ and X$^2$ are each independently selected from Cl, Br, I, OTf, OTs, OMs or OBs;
R$^1$ represents up to 3 optional ring substituent groups, which can be the same or different and are selected from —C$_1$-C$_6$ alkyl, halo, —OR$^5$, —C(O)R$^5$, —C(O)$_2$R$^5$, —NHC(O)R$^5$, —C(O)N(R$^5$)$_2$, —SR$^5$, —C$_1$-C$_6$ hydroxyalkyl, —C$_1$-C$_6$ haloalkyl, —N(R$^5$)$_2$, —S(O)R$^5$, —S(O)$_2$R$^5$, —CN and —NO$_2$;
R$^2$ represents up to 3 optional ring substituent groups, which can be the same or different and are selected from —C$_1$-C$_6$ alkyl, halo, —OR$^5$, —C(O)R$^5$, —C(O)$_2$R$^5$, —NHC(O)R$^5$, —C(O)N(R$^5$)$_2$, —SR$^5$, —C$_1$-C$_6$ hydroxyalkyl, —C$_1$-C$_6$ haloalkyl, —N(R$^5$)$_2$, —S(O)R$^5$, —S(O)$_2$R$^5$, —CN and —NO$_2$;
R$^3$ is C$_1$-C$_6$ alkyl, C$_6$-C$_{10}$ aryl, 5 or 6-membered monocyclic heteroaryl or 9 or 10-membered bicyclic heteroaryl, wherein said C$_6$-C$_{10}$ aryl group, said 5 or 6-membered monocyclic heteroaryl group and said 9 or 10-membered bicyclic heteroaryl group can each be optionally and independently substituted with up to 3 groups, each independently selected from C$_1$-C$_6$ alkyl, C$_3$-C$_7$ cycloalkyl, halo, —OR$^5$, —C(O)R$^5$, —C(O)$_2$R$^5$, —NHC(O)R$^5$, —C(O)N(R$^5$)$_2$, —SR$^5$, —C$_1$-C$_6$ hydroxyalkyl, —C$_1$-C$_6$ haloalkyl, —N(R$^5$)$_2$, —S(O)R$^5$, —S(O)$_2$R$^5$, —CN and —NO$_2$; and
R$^4$ is selected from Br, Cl, I, —OTf, —OMs, —OTs, —OBs, and —OS(O)$_2$R$^5$; and
each occurrence of R$^5$ is independently selected from H, —C$_1$-C$_6$ alkyl, C$_3$-C$_7$ cycloalkyl, C$_6$-C$_{10}$ aryl, 5 or 6-membered monocyclic heteroaryl and 9 or 10-membered bicyclic heteroaryl.

2. The compound of claim 1 having the structure:

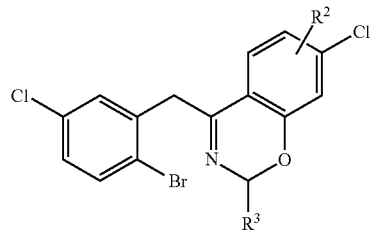

or a pharmaceutically acceptable salt thereof,
wherein:
R$^2$ represents an optional ring substituent group, which is —C$_1$-C$_6$ alkyl or halo; and
R$^3$ is C$_6$-C$_{10}$ aryl or 5 or 6-membered monocyclic heteroaryl wherein said C$_6$-C$_{10}$ aryl group and said 5 or 6-membered monocyclic heteroaryl can each be optionally and independently substituted with C$_1$-C$_6$ alkyl, halo or C$_3$-C$_7$ cycloalkyl.

3. The compound of claim 1, having the structure:

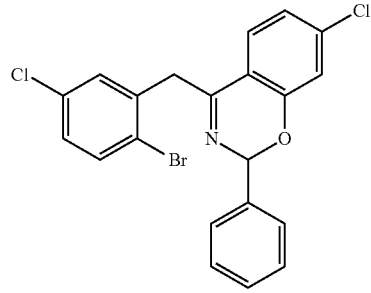

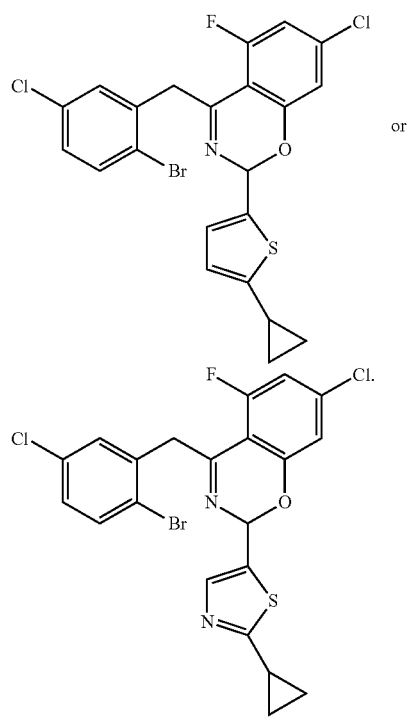
or
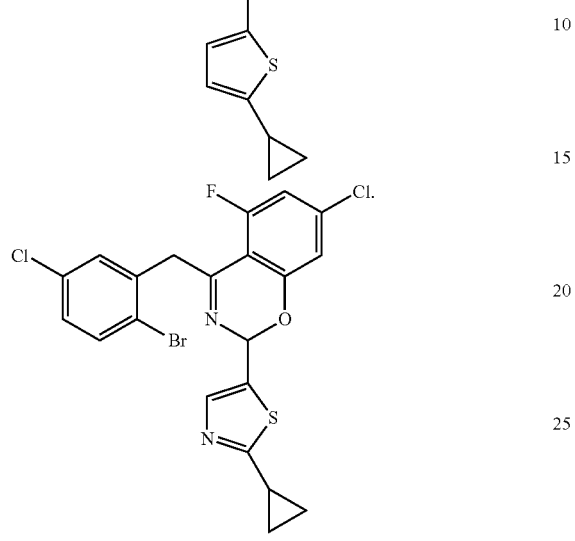
* * * * *